United States Patent [19]

Wexler

[11] Patent Number: 4,715,885
[45] Date of Patent: Dec. 29, 1987

[54] HERBICIDAL PYRAZOLE SULFONYLUREAS

[75] Inventor: Barry A. Wexler, Wilmington, Del.

[73] Assignee: E. I. Du Pont de Nemours and Company, Wilmington, Del.

[21] Appl. No.: 890,711

[22] Filed: Sep. 10, 1986

Related U.S. Application Data

[63] Continuation-in-part of Ser. No. 678,409, Dec. 10, 1984, Pat. No. 4,622,062, which is a continuation-in-part of Ser. No. 578,344, Feb. 9, 1984, abandoned.

[51] Int. Cl.[4] .................. C07D 403/12; C07D 405/12; C07D 417/12; A01N 43/66

[52] U.S. Cl. ........................................ 71/91; 544/212; 544/207; 544/209; 544/320; 544/321; 544/331; 544/219; 544/48; 71/90; 71/93

[58] Field of Search ............... 71/93, 91, 90; 544/212, 544/207, 209, 219, 48

[56] References Cited

U.S. PATENT DOCUMENTS 4,634,465  1/1987  Ehrenfreund et al. ................. 71/93

Primary Examiner—John M. Ford

[57] ABSTRACT

Pyrazole sulfonylureas are expected to show pre- and post-emergence herbicidal activity. Specifically preferred in this class of compounds is N-[(4,6-dimethoxypyrimidin-2-yl)aminocarbonyl]-4,6-dihydro-2-methyl-4-oxo-2H-furo[3,4-c]pyrazole-3-sulfonamide.

45 Claims, No Drawings

HERBICIDAL PYRAZOLE SULFONYLUREAS

BACKGROUND OF THE INVENTION

This invention relates to novel pyrazole sulfonylureas which are expected to be useful as pre- and post-emergence herbicides. In addition, some of the sulfonylureas should show selective herbicidal activity.

Herbicidal sulfonylureas are generally disclosed in U.S. Pat. Nos. 4,127,405 and 4,167,719.

U.S. Pat. No. 486,042 discloses herbicidal imidazole and pyrazole sulfonylureas such as:

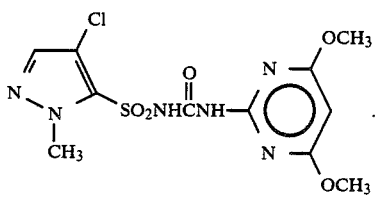

EP-A-79,683 discloses benzofuran sulfonylureas such as:

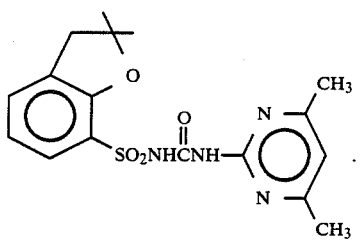

U.S. Pat. No. 533,341 teaches sulfonylureas such as:

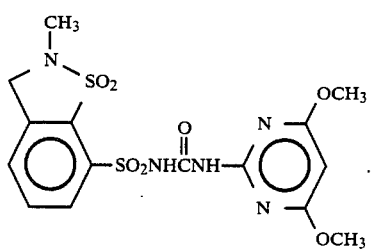

EP-A-87,780 (published 9/7/83) filed by Nissan Chemical Industries teaches pyrazole sulfonylureas of the following general formula.

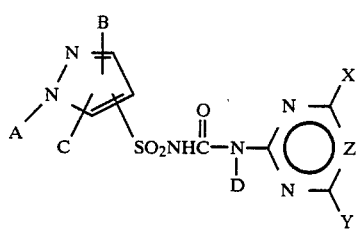

wherein
A is H, $C_1$-$C_8$ alkyl or optionally substituted phenyl;
B and C are independently H, halogen, $C_1$-$C_8$ alkyl, $CO_2R$, $SO_2NR_4R_5$, etc.
D is H or $C_1$-$C_8$ alkyl;
X and Y are independently H, halogen, $C_1$-$C_8$ alkyl, $C_1$-$C_8$ alkoxy, etc.; and
Z is C—$R_8$ or N.

The presence of undesired vegetation causes substantial damage to useful crops, especially agricultural products that satisfy man's basic food needs, such as soybeans, barley, wheat and the like. The current population explosion and the concomitant world food shortage demand improvements in the efficiency of producing these crops. Preventing or minimizing the loss of a portion of a valuable crop by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, agriculturally suitable compositions containing them and their method-of-use as pre-emergent and/or post-emergent herbicides or plant growth regulants.

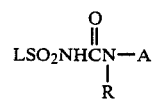

wherein
R is H or $CH_3$;
L is

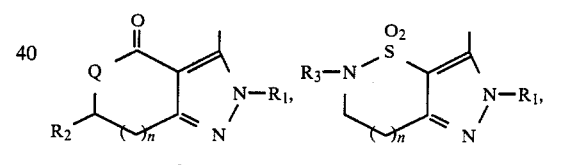

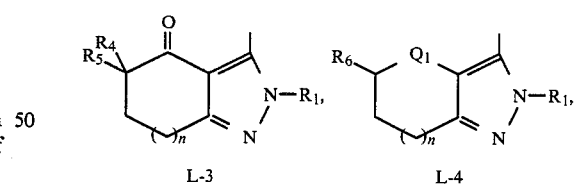

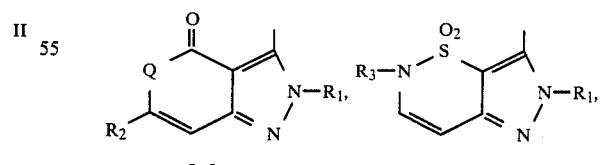

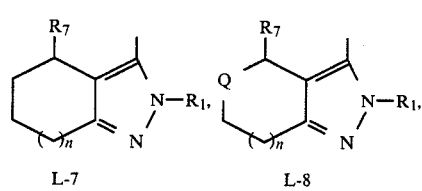

-continued

L-9, L-10, L-11, L-12, L-13, L-14, L-15, L-16, L-17, L-18, L-19, L-20

$R_1$ is H, $C_1$-$C_3$ alkyl, $CH_2CH=CH_2$, $CH_2C\equiv CH$, $CH_2CF_3$, $CHF_2$, phenyl, phenyl substituted with $NO_2$, $CH_3$, $OCH_3$, Cl, Br or F, $$-\overset{O}{\underset{\|}{C}}CH_3,$$

$SO_2CH_3$, $SO_2N(CH_3)_2$ or $CO_2CH_3$;
$R_2$ is H or $C_1$-$C_3$ alkyl;
$R_3$ is H, $C_1$-$C_3$ alkyl or $CHF_2$;
$R_4$ is H, Cl or $CH_3$;
$R_5$ is H, Cl or $CH_3$;
$R_6$ is H or $C_1$-$C_3$ alkyl;
$R_7$ is H or $CH_3$;

n is 0 or 1;
Q is O, S or $NCH_3$;
$Q_1$ is O, S or $SO_2$;
A is

A-1, A-2, A-3, A-4, A-5, A-6

X is $CH_3$, $OCH_3$, $OC_2H_5$, F, Cl, Br, $CF_3$, $OCF_2H$ or $CFH_2$;
Y is H, $C_1$-$C_3$ alkyl, $OCH_3$, $OCH_2CH_3$, $CH_2OCH_3$, $SeCH_3$, $CH_2OCH_2CH_3$, $NH_2$, $NHCH_3$, $N(CH_3)_2$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$, cyclopropyl, $CR_8(WCH_3)_2$, or $CR_8(WCH_2CH_3)_2$;
$R_8$ is H or $CH_3$;
W is O or S;
Z is CH or N;
$Y_1$ is $CH_2$ or O;
$X_1$ is $CH_3$, $OCH_3$, $OCH_2CH_3$ or $OCF_2H$;
$Y_2$ is H or $CH_3$;
$X_2$ is $CH_3$, $CH_2CH_3$ or $CH_2CF_3$;
$Y_3$ is $OCH_3$, $OCH_2CH_3$, $SCH_3$, $CH_3$ or $CH_2CH_3$;
$X_3$ is $CH_3$ or $OCH_3$;
provided that when X is Cl, F or Br, then Z is CH and Y is $OCH_3$, $OCH_2CH_3$, $NH_2$, $NHCH_3$, $N(CH_3)_2$ or $OCF_2H$; when Y is $SeCH_3$, then X is $CH_3$, $OCH_3$, $OCH_2CH_3$, $OCF_2H$ or $CF_3$; and when X or Y is $OCF_2H$, then Z is CH.

Preferred for reasons of their expected higher herbicidal activity, greater plant growth regulant activity or more favorable ease of synthesis are:
(1) Compounds of Formula I where A is A-1 and R is H.
(2) Compounds of Preferred 1 where X is $CH_3$, $OCH_3$ or Cl and Y is $C_1$-$C_3$ alkyl, $OCH_3$, $OC_2H_5$, $CH_2OCH_3$, $CF_3$, $OCH_2CF_3$, $CH(OCH_3)_2$, or cyclopropyl.

(3) Compounds of Preferred 2 where L is L-1, L-2, L-3, L-4, L-5, L-6, L-7, L-8, L-9 or L-10.
(4) Compounds of Preferred 3 where $R_1$ is H or $C_1$–$C_3$ alkyl, $R_2$ is H or $CH_3$, $R_3$ is $CH_3$, $R_4$ is H or $CH_3$, $R_5$ is H or $CH_3$, $R_6$ is H or $CH_3$, $R_7$ is H and Q is O.
(5) Compounds of Preferred 4 where L is L-1.
(6) Compounds of Preferred 4 where L is L-2.
(7) Compounds of Preferred 4 where L is L-3.
(8) Compounds of Preferred 4 where L is L-4.
(9) Compounds of Preferred 4 where L is L-5.
(10) Compounds of Preferred 4 where L is L-6.
(11) Compounds of Preferred 4 where L is L-7.
(12) Compounds of Preferred 4 where L is L-8.
(13) Compounds of Preferred 4 where L is L-9.
(14) Compounds of Preferred 4 where L is L-10.

Specifically preferred for reasons of their expected highest herbicidal activity, greatest plant growth regulant activity or most favorable ease of synthesis are:

N-[(4,6-dimethoxypyrimidin-2-yl)aminocarbonyl]-4,6-dihydro-2-methyl-4-oxo-2H-furo[3,4-c]pyrazole-3-sulfonamide; and N-[(4,6-dimethoxypyrimidin-2-yl)aminocarbonyl]-2,4,6,7-tetrahydro-2-methyl-4-oxopyrano[4,3-c]pyrazole-3-sulfonamide.

DETAILED DESCRIPTION OF THE INVENTION

Synthesis

Compounds of the Invention

The sulfonylureas of Formula I may be prepared by a number of methods. These methods are described below, along with the appropriate references for greater detail.

Equation 1

RNHA + LSO$_2$NCO $\xrightarrow[\text{24 hours}]{25-80°}$ I

II      III

U.S. Pat. Nos. 4,127,405, 4,257,802 and 4,221,585 disclose these equations and are herein incorporated by reference.

Equation 2

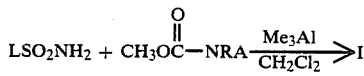

LSO$_2$NH$_2$ + CH$_3$O$\overset{\text{O}}{\overset{\|}{\text{C}}}$—NRA $\xrightarrow[\text{CH}_2\text{Cl}_2]{\text{Me}_3\text{Al}}$ I

IV     V

This reaction is taught in EPO Publication No. 83,975 (published July 20, 1983).

Equation 3

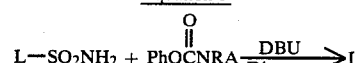

L—SO$_2$NH$_2$ + PhO$\overset{\text{O}}{\overset{\|}{\text{C}}}$NRA $\xrightarrow[\text{Dioxane}]{\text{DBU}}$ I

IV     VI

The reaction is taught in EPO Publication No. 44,807 (published Jan. 27, 1982).

Compounds of Formula I, wherein L is L-1, L-3, L-11, L-13, L-15 and L-19 are best prepared by the procedure outlined in Equation 3. All other values of L may be prepared equally well by any of the three methods taught in Equations 1-3.

INTERMEDIATE COMPOUNDS

Heterocyclic sulfonyl isocyanates of Formula III may be prepared by procedures taught in U.S. Pat. No. 4,127,405.

Heterocyclic amines of Formula II may be prepared from procedures taught in U.S. Pat. No. 4,127,405 and U.S. Pat. No. 4,221,585.

Heterocyclic carbamates of Formula V are prepared by procedures taught in EPO Publication No. 83,975. The heterocyclic carbamates of Formula VI may be prepared by procedures taught in EPO No. 44,807 and references cited therein.

Sulfonamides of Formula VII in which L is L-1 or L-11 and $R_1$, $R_2$, Q and n are as previously defined are prepared as outlined in Equations 4, 4a and 5.

Equation 4

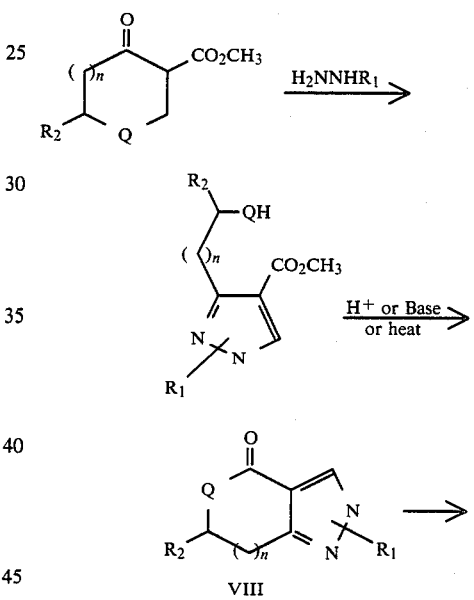

Equation 4a

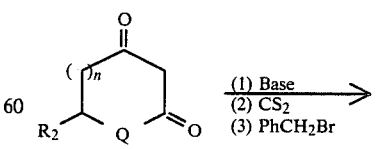

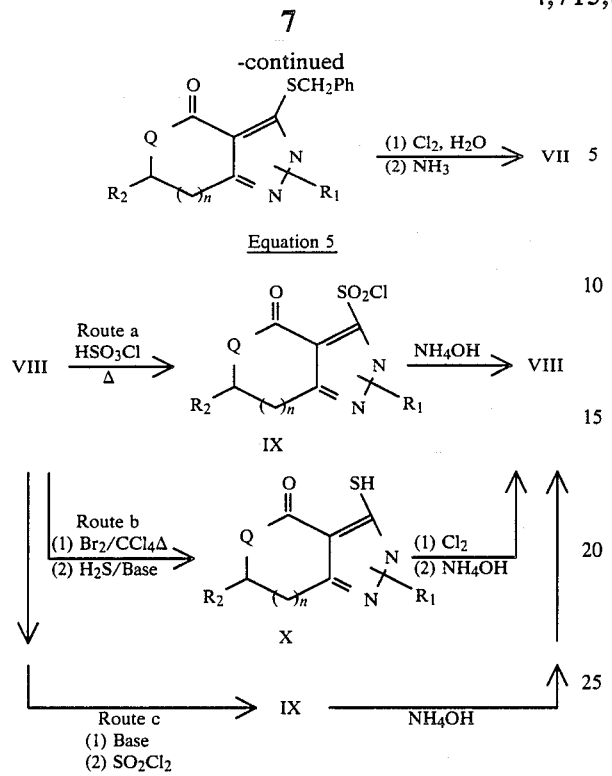

Equation 5

The conditions for carrying out the transformation in Equation 4 are known in the art. For example, see S. Gelin, B. Chantegrel and C. Deshayes, *J. Het. Chem.*, 19, 989 (1982). Preparation of sulfonamide VII from the intermediate bicyclo pyrazole VIII may be achieved in several ways as outlined in Equation 5. For example in Route a, sulfonamide VII is prepared by contacting the bicyclic pyrazole VIII with chlorosulfonic acid at the reflux point followed by amination of the resulting sulfonyl chloride IX. For further examples of chlorosulfonation of heterocycles, see Clark, et al., *Org. Syn. Coll.* Vol. 1, 2nd Ed, 1941, p. 85. An alternate route to sulfonamide VII may be achieved as shown in Route b. Bicyclic pyrazole VIII is converted to the corresponding bromide which is then contacted with hydrogen sulfide to give thiol X. Oxidation of thiol X with $Cl_2$ to the sulfonyl chloride and contacting of the sulfonyl chloride with ammonium hydroxide would then result in sulfonamide VII. Procedures for the conversion of thiols to sulfonamides are known in the art. For example, see R. O. Roblin and J. W. Clapp, *J. Am. Chem. Soc.*, 72, 4890 (1950). A third alternative which may be used to prepare sulfonamide VII from bicyclic pyrazole VIII is shown in Route C. The procedure for the lithiation of pyrazoles is known in the art. Details may be found in J. Stowell, *Carbanions in Organic Synthesis*, John Wiley and Sons, New York (1979).

Alternatively, sulfonamide VII may be prepared as outlined in Equation 4a. Conversion of the β-ketolactone to its salt, by reaction with base, followed by reaction with carbon disulfide and subsequent reaction with an alkyl or aryl halide produces the ketenethioacetal of Equation 4a. Reaction of the ketenethioacetal with hyrazine or its derivatives yields the corresponding pyrazole, which is readily converted to sulfonamide VII via oxidative chlorination and subsequent amination.

Sulfonamides of Formula XI where L is L-5 and L-15 and $R_1$, $R_2$ and Q are as previously defined may be prepared by the procedure outlined in Equation 6.

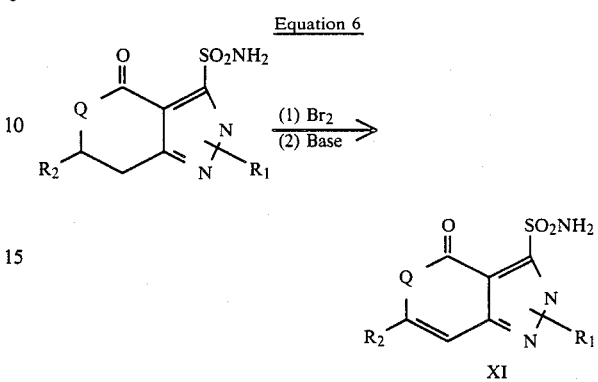

This method of halogenation, dehydrohalogenation is known in the art. For example, see *J. Org. Chem.*, 28, 1976 (1963).

Preparation of sulfonamide XII where L is L-3 and L-13 and $R_1$, $R_4$, $R_5$ and n are as previously defined is shown in Equation 7.

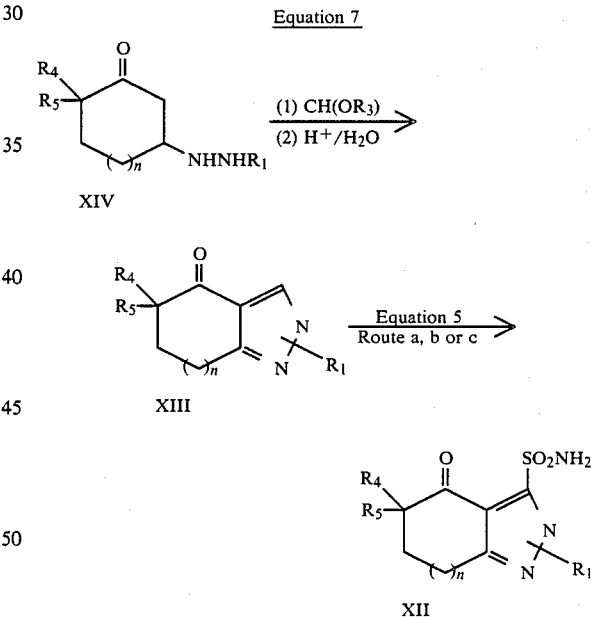

The prerequisite bicyclic pyrazole XIII is known in the art and may be prepared from hydrazone XIV as detailed by R. Borch and R. Newell, *J. Org. Chem.*, 38, 2729 (1973). For further references for the preparation of XIII, see B. Renate, *Chem. Ber.*, 100 (4), 1353-66 (1967). Conversion of bicyclic pyrazole XIII to sulfonamide XII may best be carried out using the procedures described previously in Equation 5.

Preparation of bicyclic sulfonamides of Formula XV where L is L-4, L-7, L-14 and L-17 and $R_1$, $R_6$, $R_7$, $Q_1$ ($Q_1$ in this example may also be $C-R_7$) and n are as previously described is outlined in Equation 8.

Equation 8

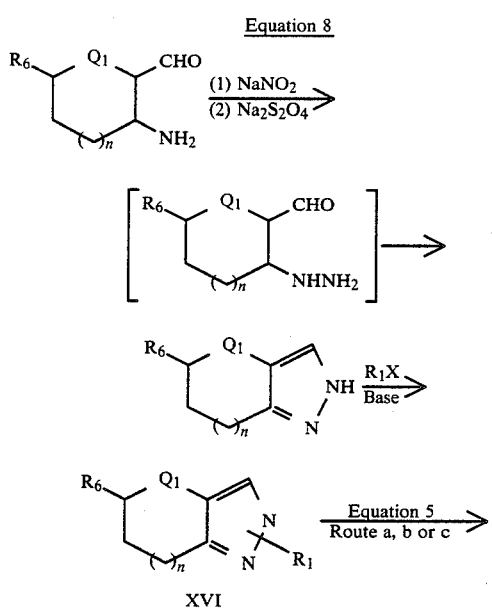

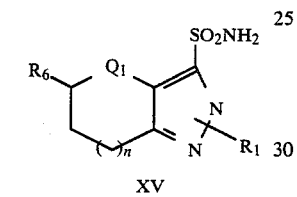

The preparation of the intermediate pyrazole XVI is known in the art and is described in V. Bauer, R. Williams, P. Richard, S. Safir, *J. Med. Chem.*, 14 (5), 454 (1971); G. Jones, J. Phipps, P. Rafferty, *Tetrahedron*, 34, 1561 (1978) and S. Gronowitz, C. Westerland, A.-B. Hornfeldt, *Chem. Scr.*, 12 (1), 1977. Functionalization of XVI to the corresponding sulfonamide XV may be accomplished using the procedures outlined previously in Equation 5.

Conversion of sulfonamide XV (where n is 0 and $R_6$ is H) to yield sulfonamide XVII where L is L-10 and L-20 is described in Equation 9.

Equation 9

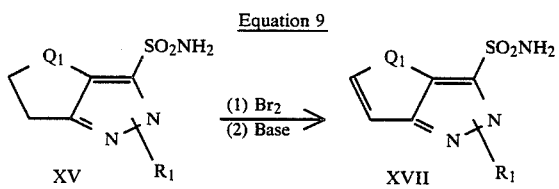

This conversion of saturated pyrazole XV to unsaturated pyrazole XVII is analogous to that described in Equation 6.

Preparation of sulfonamides XVIII where L is L-8 and L-18 and $R_1$, $R_7$, Q and n are as previously defined is outlined in Equation 10.

Equation 10

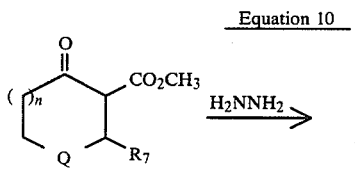

Equation 10 -continued

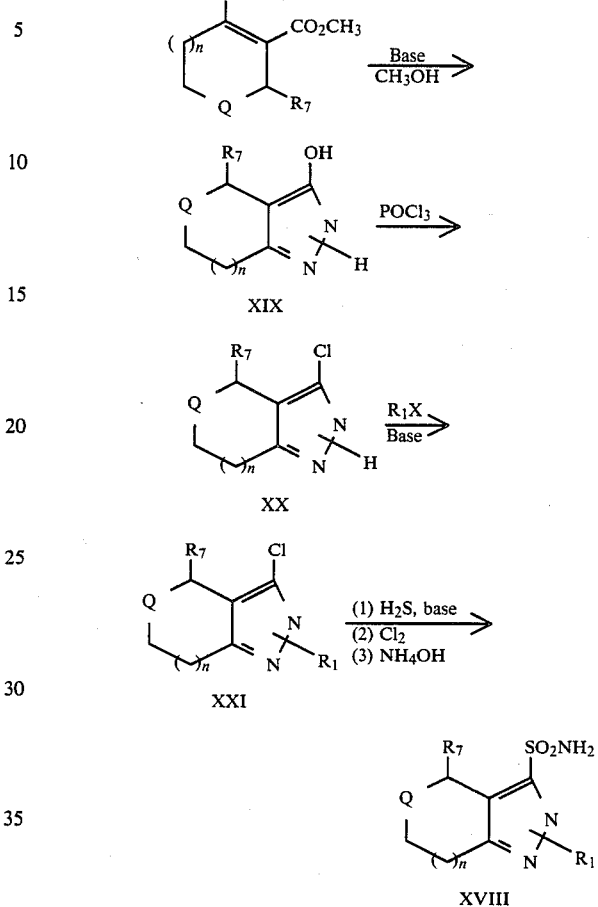

The preparation of bicyclic pyrazole XIX is known in the art and is described in V. Bauer, R. Williams and S. Safir, *J. Med. Chem.*, 14, 454 (1971).

Conversion of alcohol XIX to chloride XX may be accomplished using procedures well known in the art. Alkylation of XX would then yield the isomeric mixture XXI which may then be converted to sulfonamide XVIII. The resulting isomeric mixture may then be separated yielding the desired sulfonamides.

The preparation of sulfonamide XXII where L is L-2 and L-12 and $R_1$, $R_3$ and n are as previously defined is outlined in Equation 11.

Equation 11

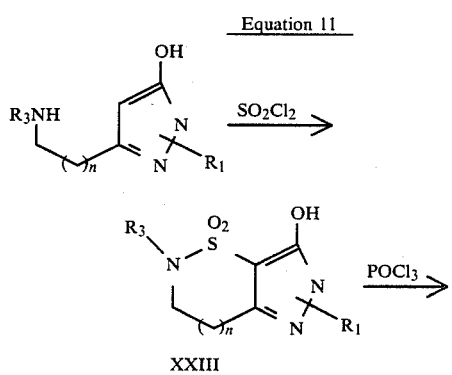

-continued
Equation 11

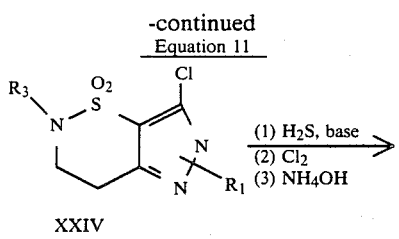

XXIV

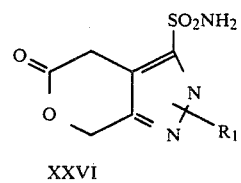

XXII

The preparation of pyrazole XXIII and conversion to chloride XXIV may be accomplished using known procedures by one skilled in the art. Conversion of XXIV to sulfonamide XXIII may best be accomplished as described above.

The preparation of sulfonamide XXV where L is L-6 or L-16 and $R_1$ and $R_3$ are as previously defined is described in Equation 12.

Equation 12

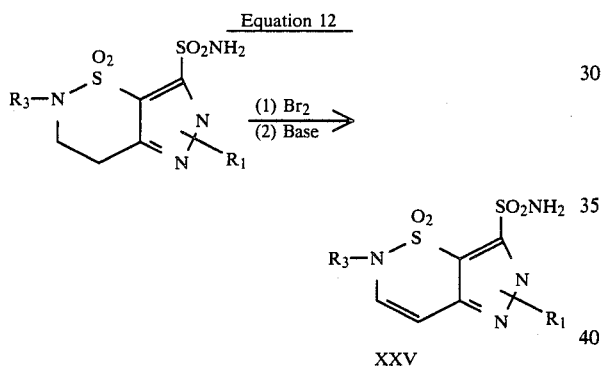

XXV

This procedure is analogous to that used in Equation 6.

Sulfonamides of Formula XXVI in which L is L-9 and L-19 and $R_1$ are as previously defined may be prepared as outlined in Equation 13.

Equation 13

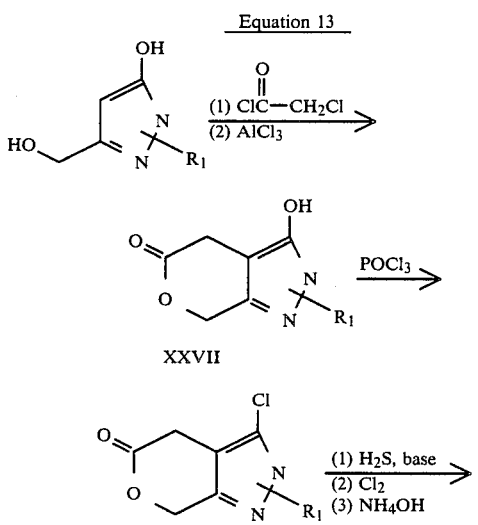

XXVII

-continued
Equation 13

XXVI

The intermediate bicyclic pyrazole XXVII is known in the art and is taught in S. Gelin, C. Deshayes, Synth., 900 (1978). Conversion of alcohol XXVII to sulfonamide XXVI may be accomplished using the procedures previously described in Equations 5 and 10.

In the following examples all parts are by weight and temperatures in °C. unless otherwise stated.

EXAMPLE 1

3-[(Bis-phenylmethylthio)methylene]-6-methyl-2H-pyran-2,4-(3H)-dione

A solution of 5,6-dihydro-4-hydroxy-6-methyl-2H-pyran-2-one (8.5 g, 66 mmol) in 25 ml of DMF was added dropwise to a suspension of NaH (5.6 g, 135 mmmols) in 50 ml DMF. After the exotherm and hydrogen evolution had ceased, a solution of $CS_2$ (5.0 ml, 80 mmols) in 25 ml DMF was added dropwise at 0° C. The resulting red solution was stirred at 0° C. until the hydrogen evolution ceased. A solution of benzyl bromide (17.5 ml, 146 mmols) in 15 ml of DMF was added dropwise at 0° C. and then allowed to stir at ambient temperature overnight. The solvent was removed in vacuo, and the residue suspended in 100 ml of $H_2O$ and 100 ml of ether. The solids were collected by filtration and recrystallized from benzene giving 9.9 g of the title compound melting at 145°-146° C.

EXAMPLE 2

1,4,6-7-Tetrahydro-1,6-dimethyl-4-oxo-3-(phenylmethylthiopyrano[4,3-c]pyrazole

Methylhydrazine (1.1 g, 23 mmol) was added in one portion to a slurry of the product from Example 1 in 25 ml of ethanol causing an exotherm and solution to occur. The reaction was refluxed for 2 hours. The solvent was removed in vacuo, and the remaining oily solid purified by medium pressure liquid chromatography (1:1 hexanes-ethyl acetate through Kieselgel 60 ®) giving 5.6 g of the title compound as an oil.

NMR (CDCl$_3$) δ: 7.26-7.06 (m, 5H, aromatic) 4.66 (m, 1H, CH$_3$CH), 4.27 (AB quartet, 2H, SCH$_2$), 3.54 (s, 3H, NCH$_3$,) 2.96-2.69 (m, 2H, CH$_3$CH(O)CH$_2$), 1.55 (d, 3H, CH$_3$CH).

EXAMPLE 3

1,4,6,7-Tetrahydro-1,6-dimethyl-4-oxopyrano[4,3-c]pyrazole-3-sulfonamide

Chlorine (4.7 ml, 97.5 mmol) was added during 5 minutes to a solution of the product from Example 2 (5.6 g, 19.5 mmol) in 90 ml of acetic acid and 0.7 ml of water (39 mmol) while keeping the temperature under 20° C. After stirring the reaction for two hours, the yellow solution was poured onto ice, and the aqueous solution washed with methylene chloride. The organic solution was separated, dried with sodium sulfate, and concentrated in vacuo giving an oil. The oil was dissolved in THF and added dropwise to a solution of 2.2 ml of ammonia (100 mmols) in 100 ml of THF causing a white solid to separate. After stirring the slurry one hour, the solid was collected by filtration, and the filtrate concentrated in vacuo giving the crude product. It was purified by medium pressure liquid chromatography (1/1 hexanes-ethyl acetate through Kieselgel 60 ®) giving 2.2 g of a solid melting at 142°–144° C.

EXAMPLE 4

N[(4,6-Dimethoxypyrimidin-2-yl)aminocarbonyl]-1,4,6,7-tetrahydro-1,6-dimethyl-4-oxopyrano[4,3-c]pyrazole-3-sulfonamide The sulfonamide from Example 3 (0.25 g, 1 mmol) in 10 ml of acetonitrile was treated with 4,6-dimethoxy-2-(phenoxycarbonyl)-aminopyrimidine (0.28 g, 1 mmol) and 1,8-diazobicyclo[5.4.0]-undec-7-ene (0.15 ml). The solution was stirred 1 hour and acidified in the cold with concentrated hydrochloric acid. The white solid that separated was collected, washed with water, and dried at 50° C. giving 370 mg of the title compound melting at 150°–152° C.

Using the procedures of Examples 1–4, and the methods described herein, the compounds of Tables I–VII may be prepared.

TABLE I

Structure: LSO₂NHC(=O)N(R)- pyrimidine with X and Y substituents

| L | R | R₁ | R₂ | R₃ | R₄ | R₅ | R₆ | R₇ | n | Q | Q₁ | X | Y | m.p. °C. |
|---|---|----|----|----|----|----|----|----|----|----|----|----|----|----------|
| L₁ | H | H | H | — | — | — | — | — | 0 | O | — | CH₃ | CH₃ | |
| L₁ | CH₃ | H | H | — | — | — | — | — | 0 | O | — | CH₃ | OCH₃ | |
| L₁ | H | CH₃ | H | — | — | — | — | — | 0 | O | — | OCH₃ | OCH₃ | |
| L₁ | H | CH₂CH₃ | H | — | — | — | — | — | 0 | O | — | CH₃ | —S-CH(−)-S- (1,3-dithiolan-2-yl) | |
| L₁ | H | CH₂CH₂CH₃ | H | — | — | — | — | — | 0 | O | — | CH₃ | OCH₃ | |
| L₁ | H | CH₂CH=CH₂ | H | — | — | — | — | — | 0 | O | — | CH₃ | OCH₃ | |
| L₁ | H | CH₂C≡CH | H | — | — | — | — | — | 0 | O | — | CH₃ | OCH₃ | |
| L₁ | H | CH₂CF₃ | H | — | — | — | — | — | 0 | O | — | CH₃ | OCH₃ | |
| L₁ | H | CHF₂ | H | — | — | — | — | — | 0 | O | — | CH₃ | OCH₃ | |
| L₁ | H | C₆H₅ (phenyl) | H | — | — | — | — | — | 0 | O | — | CH₃ | OCH₃ | |
| L₁ | H | —C(=O)CH₃ | H | — | — | — | — | — | 0 | O | — | CH₃ | OCH₃ | |
| L₁ | H | H | H | — | — | — | — | — | 1 | O | — | CH₃ | SCH₃ | |
| L₁ | H | CH₃ | H | — | — | — | — | — | 1 | O | — | OCH₃ | OCH₃ | |
| L₁ | H | CH₂CH₃ | CH₂CH₃ | — | — | — | — | — | 1 | O | — | CH₃ | CH₃ | |
| L₁ | H | CH₂CH₂CH₃ | CH₂CH₂CH₃ | — | — | — | — | — | 1 | NCH₃ | — | CH₃ | OCH₃ | |
| L₁ | H | CH₂CH=CH₂ | CH₃ | — | — | — | — | — | 1 | O | — | CH₃ | OCH₃ | |
| L₁ | H | CH₂C≡CH | CH₃ | — | — | — | — | — | 1 | O | — | CH₃ | OCH₃ | |
| L₁ | H | CH₂CF₃ | H | — | — | — | — | — | 1 | O | — | CH₃ | OCH₃ | |
| L₁ | H | CHF₂ | H | — | — | — | — | — | 1 | O | — | CH₃ | OCH₃ | |
| L₁ | H | 4-Cl-C₆H₄ | CH₃ | — | — | — | — | — | 1 | S | — | CH₃ | OCH₃ | |

TABLE I-continued

Structure: LSO₂NHC(O)NR—[pyrimidine/triazine with X and Y]

| L | R | R₁ | R₂ | R₃ | R₄ | R₅ | R₆ | R₇ | n | Q | Q₁ | X | Y | m.p. °C |
|---|---|----|----|----|----|----|----|----|---|---|----|---|---|---------|
| L₁ | H | —C(O)CH₃ | H | — | — | — | — | — | 1 | O | — | CH₃ | OCH₃ | |
| L₁ | H | SO₂CH₃ | H | — | — | — | — | — | 0 | O | — | CH₃ | CH₃ | |
| L₁ | H | SO₂CH₃ | CH₃ | — | — | — | — | — | 1 | S | — | CH₃ | OCH₃ | |
| L₁ | H | SO₂N(CH₃)₂ | H | — | — | — | — | — | 0 | O | — | OCH₃ | OCH₃ | |
| L₁ | H | SO₂N(CH₃)₂ | CH₃ | — | — | — | — | — | 1 | O | — | OCH₃ | OCH₃ | |
| L₁ | H | CO₂CH₃ | CH₃ | CHF₂ | — | — | — | — | 0 | O | — | OCH₃ | OCH₃ | |
| L₁ | H | CO₂CH₃ | CH₃ | CH₂CH₃ | — | — | — | — | 1 | O | — | OCH₃ | OCH₂CH=CH₂ | |
| L₂ | H | H | — | CH₂CH₂CH₃ | — | — | — | — | 0 | — | — | CH₃ | OCH₃ | |
| L₂ | H | CH₃ | — | H | — | — | — | — | 0 | — | — | Cl | CH(OCH₃)₂ | |
| L₂ | H | CH₂CH₃ | — | CH₃ | — | — | — | — | 0 | — | — | CH₃ | OCH₃ | |
| L₂ | H | CH₂CH₂CH₃ | — | CH₃ | — | — | — | — | 1 | — | — | CH₃ | OCH₃ | |
| L₂ | H | CH₂CH=CH₂ | — | — | — | — | — | — | 1 | — | — | CH₃ | OCH₃ | |
| L₂ | H | CH₂C≡CH | — | — | — | — | — | — | 1 | — | — | CH₃ | OCH₃ | |
| L₂ | H | CH₂CF₃ | — | — | — | — | — | — | 1 | — | — | CH₃ | OCH₃ | |
| L₂ | H | CHF₂ | — | CH₃ | — | — | — | — | 1 | — | — | CH₃ | OCH₃ | |
| L₂ | H | (4-methylphenyl) | — | CH₃ | — | — | — | — | 1 | — | — | CH₃ | OCF₂H | |
| L₂ | H | (4-methyl-2-methoxyphenyl) | — | CH₃ | — | — | — | — | 1 | — | — | CH₃ | OCH₃ | |
| L₂ | CH₃ | —C(O)CH₃ | — | CH₃ | — | — | — | — | 1 | — | — | CH₃ | OCH₃ | |
| L₂ | H | SO₂CH₃ | — | CH₃ | Cl | Cl | — | — | 0 | — | — | CH₃ | OCH₃ | |
| L₂ | H | SO₂N(CH₃)₂ | — | CH₃ | CH₃ | CH₃ | — | — | 0 | — | — | CH₃ | OCH₃ | |
| L₃ | H | CO₂CH₃ | — | CH₃ | H | H | — | — | 0 | — | — | CH₃ | OCH₃ | |
| L₃ | H | CH₃ | — | — | H | H | — | — | 0 | — | — | CH₃ | OCH₂C≡CH | |
| L₃ | H | CH₃ | — | — | — | — | — | — | 0 | — | — | CH₃ | OCH₃ | |
| L₃ | H | CH₃ | — | — | — | — | — | — | 0 | — | — | CH₃ | OCH₃ | |
| L₃ | H | CH₃ | — | — | — | — | — | — | 0 | — | — | CH₃ | OCH₃ | |
| L₃ | H | CH₂CF₃ | — | — | — | — | — | — | 1 | — | — | CH₃ | OCH₃ | |

TABLE I-continued
| L | R | R1 | R2 | R3 | R4 | R5 | R6 | R7 | n | Q | Q1 | X | Y | m.p. °C. |
|---|---|---|---|---|---|---|---|---|---|---|---|---|---|---|
| L3 | H | CH3 | — | — | H | H | — | — | — | — | — | CH3 |  | |
| L3 | H |  | — | — | H | CH3 | — | — | — | — | — | CH3 | OCH3 | |
| L3 | H |  | — | — | CH3 | Cl | — | — | — | — | — | CH3 | OCH3 | |
| L3 | H |  | — | — | CH3 | CH3 | — | — | — | — | — | CH3 | OCH3 | |
| L3 | H | CO2CH3 | — | — | CH3 | Cl | — | — | — | — | — | CH3 | OCH3 | |
| L3 | H | SO2CH3 | — | — | CH3 | CH3 | — | — | — | — | — | CH3 | OCH3 | |
| L3 | H | CO2CH3 | — | — | H | H | — | — | — | — | — | CH3 | OCH3 | |
| L3 | H | CO2CH3 | — | — | CH3 | Cl | — | — | — | — | — | CH3 | OCH3 | |
| L3 | H | CO2CH3 | — | — | CH3 | CH3 | — | — | — | — | — | CH3 | OCH3 | |
| L3 | H | CO2CH3 | — | — | CH3 | CH3 | — | — | — | — | — | CH3 | OCH3 | |
| L4 | H | CH3 | — | — | — | — | H | — | 0 | — | O | CH3 | OCH2CF3 | |
| L4 | CH3 | CH3 | — | — | — | — | H | — | 0 | — | O | CH3 | OCH3 | |
| L4 | H | CH3 | — | — | — | — | CH3 | — | 0 | — | O | OCH3 | OCH3 | |
| L4 | H | CH3 | — | — | — | — | CH3 | — | 1 | — | O | OCH3 | OCH3 | |
| L4 | H | CH3 | — | — | — | — | CH3 | — | 0 | — | O | CH3 |  | |

TABLE I-continued

Structure: LSO₂NHC(O)N(R)—[pyrimidine with X at position and Y at position]

| L | R | R₁ | R₂ | R₃ | R₄ | R₅ | R₆ | R₇ | n | Q | Q₁ | X | Y | m.p. °C. |
|---|---|----|----|----|----|----|----|----|----|----|----|----|----|----|
| L₄ | H | CH₃ | — | — | — | — | CH₂CH₃ | — | 0 | — | S | CH₃ | OCH₃ | |
| L₄ | H | CH₃ | — | — | — | — | CH₂CH₃ | — | 1 | — | SO₂ | CH₃ | OCH₃ | |
| L₄ | H | CH₃ | — | — | — | — | CH₂CH₃ | — | 1 | — | O | CH₃ | OCH₃ | |
| L₄ | H | CH₃ | — | — | — | — | CH₂CH₃ | — | 1 | — | SO₂ | CH₃ | OCH₃ | |
| L₄ | H | CH₃ | — | — | — | — | CH₂CH₃ | — | 1 | — | SO₂ | CF₃ | SeCH₃ | |
| L₅ | H | H | H | — | — | — | — | — | — | O | — | CH₃ | OCH₂CH₂OCH₃ | |
| L₅ | H | H | H | — | — | — | — | — | — | S | — | CH₃ | OCH₃ | |
| L₅ | H | H | H | — | — | — | — | — | — | NCH₃ | — | CH₃ | OCH₃ | |
| L₅ | H | CH₃ | CH₃ | — | — | — | — | — | — | O | — | CH₃ | S—C(CH₃)₂—S (cyclic) | |
| L₅ | H | H | H | — | — | — | — | — | — | NCH₃ | — | CH₃ | OCH₃ | |
| L₅ | H | Ph | H | — | — | — | — | — | — | O | — | CH₃ | OCH₃ | |
| L₅ | H | 4-NO₂-C₆H₄ | CH₃ | — | — | — | — | — | — | NCH₃ | — | CH₃ | OCH₃ | |
| L₅ | H | 4-CH₃-C₆H₄ | CH₃ | — | — | — | — | — | — | O | — | F | N(CH₃)₂ | |
| L₅ | H | Ph | CH₂CH₃ | — | — | — | — | — | — | O | — | CH₃ | OCH₃ | |
| L₅ | H | SO₂N(CH₃)₂ | CH₃ | — | — | — | — | — | — | O | — | CH₃ | OCH₃ | |

TABLE I-continued

LSO₂NHCN(R)— with pyrimidine bearing X and Y

| L | R | R₁ | R₂ | R₃ | R₄ | R₅ | R₆ | R₇ | n | Q | Q₁ | X | Y | m.p. °C. |
|---|---|---|---|---|---|---|---|---|---|---|---|---|---|---|
| L₅ | H | CO₂CH₃ | H | — | — | — | — | — | — | O | — | CH₃ | OCH₃ | |
| L₅ | H | CO₂CH₃ | CH₃ | — | — | — | — | — | — | S | — | CH₃ | OCH₃ | |
| L₅ | H | CO₂CH₃ | CH₂CH=CH₂ | — | — | — | — | — | — | O | — | CH₃ | OCH₃ | |
| L₅ | H | CO₂CH₃ | CH₂C≡CH | — | — | — | — | — | — | O | — | CH₃ | OCH₃ | |
| L₅ | H | CH₂CH₃ | CH₃ | — | — | — | — | — | — | O | — | CH₃ | OCH₃ | |
| L₅ | H | CH₂CH₃ | CH₃ | — | — | — | — | — | — | NCH₃ | — | CH₃ | OCH₃ | |
| L₆ | H | H | — | H | — | — | — | — | — | — | — | Br | OCH₂CH₃ | |
| L₆ | H | CH₃ | — | H | — | — | — | — | — | — | — | CHF₂ | OCH₃ | |
| L₆ | H | CH₃ | — | CH₃ | — | — | — | — | — | — | — | CH₃ | CH₂OCH₃ | |
| L₆ | H | CH₂CH₃ | — | CH₂CH₃ | — | — | — | — | — | — | — | CH₃ | OCH₃ | |
| L₆ | H | CH₂CH₃ | — | CH₂CH₂CH₃ | — | — | — | — | — | — | — | CH₃ | OCH₃ | |
| L₆ | H | CH₂CH₂CH₃ | — | CH₃ | — | — | — | — | — | — | — | CH₃ | OCH₃ | |
| L₆ | H | CH₂CH=CH₂ | — | CH₃ | — | — | — | — | — | — | — | CH₃ | OCH₃ | |
| L₆ | H | CH₂C≡CH | — | CH₃ | — | — | — | — | — | — | — | CH₃ | OCH₃ | |
| L₆ | H | CH₂CF₃ | — | CH₃ | — | — | — | — | — | — | — | CH₃ | OCH₃ | |
| L₆ | H | CHF₂ | — | CH₃ | — | — | — | — | — | — | — | CH₃ | OCH₃ | |
| L₆ | CH₃ | ⟨phenyl⟩ | — | CH₃ | — | — | — | — | — | — | — | CH₃ | OCH₃ | |
| L₆ | H | —C(O)CH₃ | — | CH₃ | — | — | — | — | — | — | — | CH₃ | OCH₃ | |
| L₆ | H | SO₂CH₃ | — | CH₃ | — | — | — | H | — | — | — | OCH₃ | OCH₃ | |
| L₆ | H | SO₂N(CH₃)₂ | — | CH₃ | — | — | — | CH₃ | — | — | — | OCH₃ | OCH₃ | |
| L₆ | H | CO₂CH₃ | — | CH₃ | — | — | — | H | — | — | — | CH₃ | CH₃ | |
| L₇ | H | CH₃ | — | CHF₂ | — | — | — | H | — | — | — | Cl | OCH₃ | |
| L₇ | H | CH₃ | — | — | — | — | — | H | 0 | — | — | CH₃ | NHCH₃ | |
| L₇ | H | CH₃ | — | — | — | — | — | — | 0 | — | — | CH₃ | CH₂OCH₂CH₃ | 175-185 |
| L₇ | H | CH₃ | — | — | — | — | — | — | 1 | — | — | OCH₃ | CH₃ | 171-175 |
| L₇ | H | ⟨phenyl⟩ | — | — | — | — | — | H | 0 | — | — | CH₃ | H | |

TABLE I-continued

Structure: LSO₂NHC(=O)N(R)—pyrimidine(X,Y)

| L | R | R₁ | R₂ | R₃ | R₄ | R₅ | R₆ | R₇ | n | Q | Q₁ | X | Y | m.p. °C |
|---|---|---|---|---|---|---|---|---|---|---|---|---|---|---|
| L₇ | H | 4-Cl-C₆H₄ | — | — | — | — | — | CH₃ | 0 | — | — | CH₃ | NH₂ | |
| L₇ | H | 4-Br-C₆H₄ | — | — | — | — | — | H | 1 | — | — | CH₃ | OCH₃ | |
| L₇ | H | 4-CH₃-C₆H₄ | — | — | — | — | — | CH₃ | 1 | — | — | CH₃ | OCH₃ | |
| L₇ | H | SO₂N(CH₃)₂ | — | — | — | — | — | H | 0 | — | — | CH₃ | OCH₃ | |
| L₇ | H | SO₂N(CH₃)₂ | — | — | — | — | — | CH₃ | 0 | — | — | CH₃ | OCH₃ | |
| L₇ | H | SO₂N(CH₃)₂ | — | — | — | — | — | H | 1 | — | — | CH₃ | OCH₃ | |
| L₇ | H | SO₂N(CH₃)₂ | — | — | — | — | — | CH₃ | 1 | — | — | CH₃ | OCH₃ | |
| L₈ | H | CH₃ | — | — | — | — | — | H | 0 | S | — | CH₃ | OCH₃ | |
| L₈ | H | CH₃ | — | — | — | — | — | H | 0 | O | — | CH₃ | CH₂CH₃ | |
| L₈ | H | CH₃ | — | — | — | — | — | CH₃ | 1 | O | — | CH₃ | OCH₃ | |
| L₈ | H | CH₂CH=CH₂ | — | — | — | — | — | H | 0 | O | — | CH₃ | OCH₃ | |
| L₈ | H | CH₂C≡CH | — | — | — | — | — | CH₃ | 1 | O | — | CH₃ | OCH₃ | |
| L₈ | H | CH₂CF₃ | — | — | — | — | — | H | 0 | O | — | CH₃ | OCH₃ | |
| L₈ | H | CH₂CF₃ | — | — | — | — | — | CH₃ | 1 | O | — | CH₃ | OCH₃ | |
| L₈ | H | CH₂CF₃ | — | — | — | — | — | H | 1 | O | — | CH₃ | OCH₃ | |
| L₈ | H | CHF₂ | — | — | — | — | — | H | 0 | O | — | CH₃ | OCH₃ | |
| L₈ | H | CHF₂ | — | — | — | — | — | CH₃ | 0 | O | — | CH₃ | OCH₃ | |
| L₈ | H | —C(=O)CH₃ | — | — | — | — | — | H | 0 | O | — | CH₃ | OCH₃ | |
| L₈ | H | —C(=O)CH₃ | — | — | — | — | — | CH₃ | 0 | O | — | CH₃ | OCH₃ | |

TABLE I-continued

LSO₂NHCN(R)—[pyrimidine with X, Y substituents]

| L | R | R₁ | R₂ | R₃ | R₄ | R₅ | R₆ | R₇ | n | Q | Q₁ | X | Y | m.p. °C. |
|---|---|---|---|---|---|---|---|---|---|---|---|---|---|---|
| L₈ | H | SO₂CH₃ | — | — | — | — | — | H | 1 | O | — | CH₃ | S-CH(CH₃)-S (cyclic) | |
| L₈ | H | SO₂CH₃ | — | — | — | — | — | CH₃ | 1 | O | — | CH₃ | OCH₃ | |
| L₈ | H | SO₂N(CH₃)₂ | — | — | — | — | — | H | 1 | O | — | CH₃ | OCH₃ | |
| L₈ | H | SO₂N(CH₃)₂ | — | — | — | — | — | CH₃ | 1 | O | — | CH₃ | OCH₃ | |
| L₈ | H | CO₂CH₃ | — | — | — | — | — | H | 1 | O | — | CH₃ | OCH₃ | |
| L₈ | H | CO₂CH₃ | — | — | — | — | — | CH₃ | 1 | O | — | CH₃ | N(CH₃)₂ | |
| L₈ | H | H | — | — | — | — | — | — | — | — | — | CH₃ | OCH₃ | |
| L₉ | H | CH₃ | — | — | — | — | — | — | — | — | — | CH₃ | S-C(CH₃)₂-S (cyclic) | |
| L₉ | H | CH₂CH=CH₂ | — | — | — | — | — | — | — | — | — | CH₃ | OCH₃ | |
| L₉ | H | CH₂C≡CH | — | — | — | — | — | — | — | — | — | CH₃ | OCH₃ | |
| L₉ | H | o-Cl-C₆H₄ | — | — | — | — | — | — | — | — | — | CH₃ | OCH₃ | |
| L₉ | H | SO₂CH₃ | — | — | — | — | — | — | — | — | — | CH₃ | OCH₃ | |
| L₉ | H | SO₂N(CH₃)₂ | — | — | — | — | — | — | — | — | — | CH₃ | OCH₃ | |
| L₉ | H | CO₂CH₃ | — | — | — | — | — | — | — | — | O | CH₃ | CH₂SCH₃ | |
| L₉ | H | H | — | — | — | — | — | — | — | — | O | CH₃ | CH(SCH₂CH₃)₂ | |
| L₁₀ | H | H | — | — | — | — | — | — | — | — | SO₂ | CH₃ | OCH₃ | |
| L₁₀ | H | CH₃ | — | — | — | — | — | — | — | — | O | CH₃ | OCH₃ | |
| L₁₀ | H | CH₃ | — | — | — | — | — | — | — | — | SO₂ | CH₃ | OCH₃ | |

TABLE I-continued

LSO₂NHCN(R)—[pyrimidine with X, Y substituents]

| L | R | R₁ | R₂ | R₃ | R₄ | R₅ | R₆ | R₇ | n | Q | Q₁ | X | Y | m.p. °C. |
|---|---|---|---|---|---|---|---|---|---|---|---|---|---|---|
| L₁₀ | H | CO₂CH₃ | — | — | — | — | — | — | — | — | O | CH₃ | OCH₃ | 206-208 |
| L₁₁ | H | CH₃ | CH₃ | — | — | — | — | — | 1 | O | — | CH₃ | OCH₃ | 200-204 |
| L₁₁ | H | CH₃ | CH₃ | — | — | — | — | — | 1 | O | — | CH₃ | OCH₃ | 150-152 |
| L₁₁ | H | CH₃ | CH₃ | — | — | — | — | — | 1 | O | — | OCH₃ | OCH₃ | 182-185 |
| L₁₁ | H | CH₃ | CH₃ | — | — | — | — | — | 1 | O | — | Cl | OCH₃ |  |
| L₁₁ | H | CH₃ | H | — | — | — | — | — | 0 | O | — | Cl | OCF₂H |  |
| L₁₁ | H | CH₃ | H | — | — | — | — | — | 1 | NCH₃ | — | CH₃ | OCH₃ |  |
| L₁₁ | H | CH₃ | CH₃ | — | — | — | — | — | 0 | S | — | CH₃ | OCH₃ |  |
| L₁₁ | H | CH₃ | CH₂CH₃ | — | — | — | — | — | 1 | NCH₃ | — | CH₃ | OCH₃ |  |
| L₁₁ | H | CH₃ | CH₂CH₃ | — | — | — | — | — | 0 | O | — | CH₃ | OCH₃ |  |
| L₁₁ | H | CH₃ | CH₂CH₂CH₃ | — | — | — | — | — | 1 | O | — | CH₃ | OCH₃ |  |
| L₁₁ | H | CH₃ | CH₂CH₂CH₃ | — | — | — | — | — | 0 | O | — | CH₃ | OCH₃ |  |
| L₁₂ | H | CH₃ | — | H | — | — | — | — | 1 | — | — | CH₃ | SCF₂H |  |
| L₁₂ | H | CH₃ | — | CH₃ | — | — | — | — | — | — | — | CH₃ | —CH(SCH₃)₂ |  |
| L₁₂ | H | CH₃ | — | CH₂CH₃ | — | — | — | — | — | — | — | CH₃ | OCH₃ |  |
| L₁₂ | H | CH₂CH=CH₂ | — | CH₂CH₂CH₃ | — | — | — | — | — | — | — | OCH₃ | OCH₃ |  |
| L₁₂ | H | CH₂CH=CH₂ | — | CH₃ | — | — | — | — | — | — | — | CH₃ | OCH₃ |  |
| L₁₂ | H | CH₂C≡CH | — | CH₃ | — | — | — | — | — | — | — | CH₃ | OCH₃ |  |
| L₁₂ | H | CH₂C≡CH | — | CH₃ | — | — | — | — | — | — | — | CH₃ | OCH₃ |  |
| L₁₂ | H | CO₂CH₃ | — | CH₃ | — | — | — | — | — | — | — | CH₃ | OCH₃ |  |
| L₁₂ | CH₃ | CO₂CH₃ | — | CH₃ | — | — | — | — | — | — | — | CH₃ | OCH₃ |  |
| L₁₂ | H | CH₃ | — | — | — | — | — | — | — | — | — | CH₃ | OCH₃ |  |
| L₁₃ | H | CH₃ | — | — | CH₃ | H | — | — | 0 | — | — | CH₃ | CH(OCH₃)₂ |  |
| L₁₃ | H | CH₃ | — | — | H | CH₃ | — | — | 1 | — | — | CH₃ | [tetrahydrofuran-2-yl] |  |
| L₁₃ | H | CH₃ | — | — | H | H | — | — | — | — | — | CH₃ | OCH₃ |  |
| L₁₃ | H | CH₃ | — | — | CH₃ | H | — | — | 0 | — | — | CH₃ | OCH₃ |  |
| L₁₃ | H | CH₃ | — | — | CH₃ | CH₃ | — | — | 1 | — | — | CH₃ | OCH₃ |  |
| L₁₃ | H | CH₃ | — | — | CH₃ | Cl | — | — | 0 | — | — | CH₃ | OCH₃ |  |
| L₁₃ | H | CH₃ | — | — | CH₃ | Cl | — | — | 1 | — | — | CH₃ | OCH₃ |  |

TABLE I-continued

Structure: LSO₂NHCN(R)—C(=O)—N=pyridine(X,Y) — represented as:

$$LSO_2NHCN(R)C(=O)-\text{pyridine}(X,Y)$$

| L | R | $R_1$ | $R_2$ | $R_3$ | $R_4$ | $R_5$ | $R_6$ | $R_7$ | n | Q | $Q_1$ | X | Y | m.p. °C |
|---|---|---|---|---|---|---|---|---|---|---|---|---|---|---|
| $L_{13}$ | H | $CH_3$ | — | — | Cl | Cl | — | — | — | — | — | $CH_3$ | $OCH_3$ | |
| $L_{14}$ | H | H | — | — | — | — | H | — | 0 | — | O | $CH_3$ | 2-methyl-1,3-dioxolane | |
| $L_{14}$ | H | H | — | — | — | — | H | — | 0 | — | O | $CH_3$ | $OCH_3$ | |
| $L_{14}$ | H | H | — | — | — | — | $CH_3$ | — | 0 | — | O | $CH_3$ | $OCH_3$ | |
| $L_{14}$ | H | H | — | — | — | — | $CH_2CH_3$ | — | 0 | — | O | $CH_3$ | $OCH_3$ | |
| $L_{14}$ | H | H | — | — | — | — | $CH_2CH_2CH_3$ | — | 0 | — | O | $CH_3$ | $OCH_3$ | |
| $L_{14}$ | H | H | — | — | — | — | H | — | 1 | — | $SO_2$ | $CH_3$ | $OCH_3$ | |
| $L_{14}$ | H | H | — | — | — | — | $CH_3$ | — | 1 | — | $SO_2$ | $CH_3$ | $OCH_3$ | |
| $L_{14}$ | H | H | — | — | — | — | $CH_2CH_3$ | — | 1 | — | $SO_2$ | $CH_3$ | $OCH_3$ | |
| $L_{14}$ | H | H | — | — | — | — | $CH_2CH_2CH_3$ | — | 1 | — | $SO_2$ | $CH_3$ | $OCH_3$ | |
| $L_{15}$ | H | $CH_3$ | H | — | — | — | — | — | 0 | O | — | $CH_3$ | 2-methyl-1,3-dioxane | |
| $L_{15}$ | H | $CH_3$ | H | — | — | — | — | — | — | O | — | $CH_3$ | $OCH_3$ | |
| $L_{15}$ | H | $CH_3$ | H | — | — | — | — | — | — | $CH_3N$ | — | $CH_3$ | $OCH_3$ | |
| $L_{15}$ | H | $CH_3$ | $CH_3$ | — | — | — | — | — | — | O | — | $CH_3$ | $OCH_3$ | |
| $L_{15}$ | H | $CH_3$ | $CH_3$ | — | — | — | — | — | — | $CH_3N$ | — | $CH_3$ | $OCH_3$ | |
| $L_{15}$ | H | $CH_3$ | $CH_2CH_3$ | — | — | — | — | — | — | O | — | $CH_3$ | $OCH_3$ | |
| $L_{16}$ | H | H | — | H | — | — | — | — | — | — | — | $CH_3$ | 2-methyl-1,3-dioxane | |
| $L_{16}$ | H | H | — | $CH_3$ | — | — | — | — | — | — | — | $CH_3$ | $OCH_3$ | |
| $L_{16}$ | H | $CH_3$ | — | $CH_3$ | — | — | — | — | — | — | — | $CH_3$ | $OCH_3$ | |
| $L_{16}$ | H | $CH_3$ | — | $CH_2CH_3$ | — | — | — | — | — | — | — | $CH_3$ | $OCH_3$ | |
| $L_{16}$ | H | $CH_3$ | — | $CHF_2$ | — | — | — | — | — | — | — | $CH_3$ | $OCH_3$ | |

TABLE I-continued

| L | R | $R_1$ | $R_2$ | $R_3$ | $R_4$ | $R_5$ | $R_6$ | $R_7$ | n | Q | $Q_1$ | X | Y | m.p. °C. |
|---|---|---|---|---|---|---|---|---|---|---|---|---|---|---|
| $L_{17}$ | H | $CH_3$ | — | — | — | — | — | H | 0 | — | — | $CH_3$ | (2-methyl-1,3-dioxolan-4-yl)methoxy | |
| $L_{17}$ | H | $CH_3$ | — | — | — | — | — | H | 0 | — | — | $CH_3$ | $OCH_3$ | 190–191 |
| $L_{17}$ | H | $CH_3$ | — | — | — | — | — | H | 1 | — | — | $CH_3$ | $OCH_3$ | 190–191 |
| $L_{17}$ | H | $CH_3$ | — | — | — | — | — | H | 1 | — | — | Cl | $OCH_3$ | 195–196 |
| $L_{17}$ | H | $CH_3$ | — | — | — | — | — | H | 1 | — | — | $CH_3$ | $CH_3$ | 202–204 |
| $L_{17}$ | H | $CH_3$ | — | — | — | — | — | $CH_3$ | 0 | — | — | $OCH_3$ | $OCH_3$ | |
| $L_{17}$ | H | $CH_3$ | — | — | — | — | — | $CH_3$ | 1 | — | — | $CH_3$ | $OCH_3$ | |
| $L_{17}$ | H | $CH_3$ | — | — | — | — | — | $CH_3$ | 1 | — | — | $OCH_3$ | $OCH_3$ | |
| $L_{18}$ | H | $CH_3$ | — | — | — | — | — | H | 0 | O | — | $CH_3$ | $CH(OCH_2CH_3)_2$ | |
| $L_{18}$ | H | $CH_3$ | — | — | — | — | — | H | 0 | $SO_2$ | — | $CH_3$ | $OCH_3$ | |
| $L_{18}$ | H | $CH_3$ | — | — | — | — | — | $CH_3$ | 0 | O | — | $CH_3$ | $OCH_3$ | |
| $L_{18}$ | H | $CH_3$ | — | — | — | — | — | H | 1 | O | — | $CH_3$ | $OCH_3$ | |
| $L_{18}$ | H | $CH_3$ | — | — | — | — | — | $CH_3$ | 1 | $SO_2$ | — | $CH_3$ | $OCH_3$ | |
| $L_{19}$ | H | H | — | — | — | — | — | — | — | — | — | $CH_3$ | $OCH_3$ | |
| $L_{19}$ | H | $CH_2CH_3$ | — | — | — | — | — | — | — | — | — | $CH_3$ | $OCH_3$ | |
| $L_{19}$ | H | $CH_2CH_2CH_3$ | — | — | — | — | — | — | — | — | — | $CH_3$ | $OCH_3$ | |
| $L_{19}$ | H | $SO_2N(CH_3)_2$ | — | — | — | — | — | — | — | — | — | $CH_3$ | $OCH_3$ | |
| $L_{19}$ | H | $CO_2CH_3$ | — | — | — | — | — | — | — | — | — | $CH_3$ | $OCH_3$ | |
| $L_{20}$ | H | $CH_3$ | — | — | — | — | — | — | — | — | $SO_2$ | $CH_3$ | $OCH_3$ | |
| $L_{20}$ | H | H | — | — | — | — | — | — | — | — | O | $CH_3$ | $OCH_3$ | |
| $L_{20}$ | H | H | — | — | — | — | — | — | — | — | $SO_2$ | $CH_3$ | $OCH_3$ | |
| $L_{20}$ | H | $SO_2CH_3$ | — | — | — | — | — | — | — | — | O | $CH_3$ | $OCH_3$ | |
| $L_{20}$ | H | $SO_2CH_3$ | — | — | — | — | — | — | — | — | $SO_2$ | $CH_3$ | $OCH_3$ | |

TABLE 2

LSO₂NHCN-[pyrimidine/triazine ring with X, Y substituents]

| L | R | R₁ | R₂ | R₃ | R₄ | R₅ | R₆ | R₇ | n | Q | Q₁ | X | Y | m.p. °C. |
|---|---|----|----|----|----|----|----|----|---|---|----|---|---|---|
| $L_1$ | H | CH₃ | H | — | — | — | — | — | 0 | O | — | CH₃ | OCH₃ | |
| $L_1$ | H | CH₃ | H | — | — | — | — | — | 1 | O | — | OCH₃ | OCH₃ | |
| $L_1$ | H | CH₃ | CH₃ | — | — | — | — | — | 0 | O | — | CH₃ | CH₃ | |
| $L_1$ | H | CH₃ | CH₃ | — | — | — | — | — | 1 | O | — | CF₃ | OCH₃ | |
| $L_1$ | H | CH₃ | H | — | — | — | — | — | 0 | NCH₃ | — | CH₃ | OCH₃ | |
| $L_1$ | H | CH₃ | H | — | — | — | — | — | 1 | NCH₃ | — | CH₃ | CH₂OCH₃ | |
| $L_1$ | H | CH₃ | CH₃ | — | — | — | — | — | 0 | NCH₃ | — | CH₃ | OCH₃ | |
| $L_1$ | H | CH₃ | CH₃ | — | — | — | — | — | 1 | NCH₃ | — | CH₃ | CH₃ | |
| $L_2$ | H | CH₃ | — | H | — | — | — | — | 0 | — | — | CH₃ | CH₃ | |
| $L_2$ | H | CH₃ | — | CH₃ | — | — | — | — | 0 | — | — | CH₃ | SeCH₃ | |
| $L_2$ | H | CH₃ | — | H | — | — | — | — | 1 | — | — | OCF₂H | OCH₃ | |
| $L_2$ | CH₃ | CH₃ | — | CH₃ | — | — | — | — | 1 | — | — | OCH₃ | OCH₃ | |
| $L_2$ | H | CH₃ | — | CHF₂ | — | — | — | — | 0 | — | — | CH₃ | OCH₃ | |
| $L_2$ | H | CH₃ | — | CHF₂ | — | — | — | — | 1 | — | — | CH₃ | CH₃ | |
| $L_3$ | H | CH₃ | — | — | H | H | — | — | 0 | — | — | CH₃ | NH₂ | |
| $L_3$ | H | CH₃ | — | — | H | H | — | — | 1 | — | — | OCH₃ | CH₃ | |
| $L_3$ | H | CH₃ | — | — | CH₃ | Cl | — | — | 0 | — | — | CH₃ | OCH₃ | |
| $L_3$ | H | CH₃ | — | — | CH₃ | Cl | — | — | 1 | — | — | CH₃ | OCH₃ | |
| $L_3$ | H | CH₃ | — | — | CH₃ | CH₃ | — | — | 0 | — | — | CH₃ | OCH₃ | |
| $L_3$ | H | CH₃ | — | — | CH₃ | CH₃ | — | — | 1 | — | — | OCH₃ | NHCH₃ | |
| $L_3$ | H | CH₃ | — | — | Cl | Cl | — | — | 0 | — | — | CH₃ | OCH₃ | |
| $L_3$ | H | CH₃ | — | — | Cl | Cl | — | — | 1 | — | — | CH₃ | OCH₃ | |
| $L_4$ | H | CH₃ | — | — | — | — | H | — | 0 | — | O | CF₃ | CH₃ | |
| $L_4$ | H | CH₃ | — | — | — | — | H | — | 1 | — | S | CH₃ | OCH₃ | |
| $L_4$ | H | CH₃ | — | — | — | — | CH₃ | — | 0 | — | SO₂ | CH₃ | OCH₃ | |
| $L_4$ | H | CH₃ | — | — | — | — | CH₃ | — | 1 | — | O | OCH₃ | CH₃ | |
| $L_5$ | H | CH₃ | H | — | — | — | — | — | — | O | — | CH₃ | OCH₃ | |
| $L_5$ | H | CH₃ | H | — | — | — | — | — | — | NCH₃ | — | OCH₃ | OCH₃ | |
| $L_5$ | H | CH₃ | CH₃ | — | — | — | — | — | — | O | — | OCH₃ | CH₃ | |
| $L_5$ | H | CH₃ | CH₃ | — | — | — | — | — | — | NCH₃ | — | CH₃ | N(CH₃)₂ | |
| $L_5$ | H | CH₃ | H | — | — | — | — | — | — | S | — | CH₃ | OCH₃ | |
| $L_5$ | H | CH₃ | CH₃ | — | — | — | — | — | — | S | — | CH₃ | OCH₃ | |
| $L_6$ | H | CH₃ | — | H | — | — | — | — | — | — | — | CF₃ | OCH₃ | |
| $L_6$ | H | CH₃ | — | CH₃ | — | — | — | — | — | — | — | CH₃ | CH₂CH₃ | |
| $L_6$ | H | CH₃ | — | CH₂CH₃ | — | — | — | — | — | — | — | OCH₃ | OCH₃ | |
| $L_6$ | CH₃ | CH₃ | — | CH₂CH₂CH₃ | — | — | — | — | — | — | — | CH₃ | OCH₃ | |
| $L_6$ | H | CH₃ | — | CHF₂ | — | — | — | — | — | — | — | OCF₂H | OCH₃ | |
| $L_6$ | H | H | — | CH₃ | — | — | — | — | — | — | — | CH₃ | OCH₃ | |
| $L_7$ | H | CH₃ | — | — | — | — | — | H | 1 | — | — | CH₃ | OCH₃ | 199–201 |
| $L_7$ | H | CH₃ | — | — | — | — | — | H | 1 | — | — | OCH₃ | OCH₃ | 204–205 |
| $L_7$ | H | H | — | — | — | — | — | CH₃ | 0 | — | — | OCH₃ | CF₃ | |
| $L_7$ | H | H | — | — | — | — | — | H | 1 | — | — | CH₃ | OCH₃ | |
| $L_7$ | H | SO₂CH₃ | — | — | — | — | — | CH₃ | 1 | — | — | CH₃ | OCH₃ | |
| $L_7$ | H | SO₂N(CH₃)₂ | — | — | — | — | — | CH₃ | 1 | — | — | OCH₃ | OCH₃ | |
| $L_8$ | H | CH₃ | — | — | — | — | — | H | 0 | — | — | CH₃ | SCH₃ | |
| $L_8$ | H | CH₃ | — | — | — | — | — | H | 1 | — | — | CH₃ | OCH₃ | |
| $L_8$ | H | CH₃ | — | — | — | — | — | CH₃ | 0 | — | — | CH₃ | OCH₃ | |
| $L_8$ | H | CH₃ | — | — | — | — | — | CH₃ | 1 | — | — | OCH₃ | CH₃ | |
| $L_8$ | H | CO₂CH₃ | — | — | — | — | — | CH₃ | 0 | — | — | CH₃ | OCH₃ | |
| $L_8$ | H | CO₂CH₃ | — | — | — | — | — | —CH₃ | 1 | — | — | CH₃ | OCH₂CH=CH₂ | |
| $L_9$ | H | H | — | — | — | — | — | — | — | — | — | OCH₃ | OCH₃ | |
| $L_9$ | H | CH₃ | — | — | — | — | — | — | — | — | — | CH₃ | OCH₃ | |
| $L_9$ | H | CH₂CH₃ | — | — | — | — | — | — | — | — | — | CH₃ | CH₃ | |
| $L_9$ | H | CH₂CH₂CH₃ | — | — | — | — | — | — | — | — | — | OCH₃ | OCH₃ | |
| $L_9$ | H | CO₂CH₃ | — | — | — | — | — | — | — | — | — | CH₃ | OCH₂C≡CH | |
| $L_9$ | H | CH₂CH=CH₂ | — | — | — | — | — | — | — | — | — | CF₃ | OCH₃ | |
| $L_9$ | H | CH₂C≡CH | — | — | — | — | — | — | — | — | — | CH₃ | OCH₃ | |
| $L_9$ | H | CH₂CF₃ | — | — | — | — | — | — | — | — | — | CH₃ | OCH₃ | |
| $L_{10}$ | H | CH₃ | — | — | — | — | — | — | — | — | O | CH₃ | OCH₃ | |
| $L_{10}$ | H | CH₃ | — | — | — | — | — | — | — | — | SO₂ | CH₃ | OCH₂CF₃ | |
| $L_{10}$ | H | CH₂CH=CH₂ | — | — | — | — | — | — | — | — | O | CH₃ | OCH₃ | |
| $L_{10}$ | H | CH₂CH=CH₂ | — | — | — | — | — | — | — | — | SO₂ | OCH₃ | OCH₃ | |
| $L_{10}$ | H | 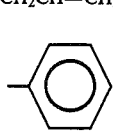 | — | — | — | — | — | — | — | — | O | OCF₂H | CH₃ | |

TABLE 2-continued

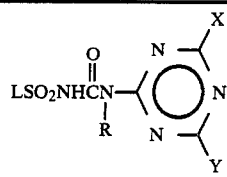

| L | R | $R_1$ | $R_2$ | $R_3$ | $R_4$ | $R_5$ | $R_6$ | $R_7$ | n | Q | $Q_1$ | X | Y | m.p. °C. |
|---|---|---|---|---|---|---|---|---|---|---|---|---|---|---|
| $L_{10}$ | H | ⌬ | — | — | — | — | — | — | — | — | $SO_2$ | $OCH_3$ | $OCH_3$ | |
| $L_{10}$ | H | $SO_2N(CH_3)_2$ | — | — | — | — | — | — | — | — | O | $CF_3$ | $OCH_3$ | |
| $L_{10}$ | H | $SO_2N(CH_3)_2$ | — | — | — | — | — | — | — | — | $SO_2$ | $CH_3$ | $CH_2SCH_3$ | |
| $L_{10}$ | H | $CO_2CH_3$ | — | — | — | — | — | — | — | — | O | $CH_3$ | $OCH_3$ | |
| $L_{10}$ | H | $CO_2CH_3$ | — | — | — | — | — | — | — | — | $SO_2$ | $OCH_3$ | $OCH_3$ | |
| $L_{11}$ | H | $CH_3$ | $CH_3$ | — | — | — | — | — | 1 | O | — | $OCH_3$ | $CH_3$ | 139–140.5 |
| $L_{11}$ | H | $CH_3$ | $CH_3$ | — | — | — | — | — | 1 | O | — | $OCH_3$ | $OCH_3$ | 185–188 |
| $L_{11}$ | H | H | H | — | — | — | — | — | 0 | O | — | $CH_3$ | $OCH_3$ | |
| $L_{11}$ | H | H | H | — | — | — | — | — | 1 | O | — | $OCH_3$ | $CH_3$ | |
| $L_{11}$ | H | H | $CH_3$ | — | — | — | — | — | 0 | O | — | $CH_3$ | $OCF_2H$ | |
| $L_{11}$ | $CH_3$ | H | $CH_3$ | — | — | — | — | — | 1 | O | — | $OCH_3$ | $OCH_3$ | |
| $L_{11}$ | H | H | H | — | — | — | — | — | 0 | $NCH_3$ | — | $CH_3$ | $OCH_3$ | |
| $L_{11}$ | H | H | H | — | — | — | — | — | 1 | $NCH_3$ | — | $CH_3$ | $CH_3$ | |
| $L_{11}$ | H | H | $CH_3$ | — | — | — | — | — | 0 | $NCH_3$ | — | $CH_3$ | $SCF_2H$ | |
| $L_{11}$ | H | H | $CH_3$ | — | — | — | — | — | 1 | $NCH_3$ | — | $CF_3$ | $OCH_3$ | |
| $L_{12}$ | H | H | — | H | — | — | — | — | — | — | — | $CH_3$ | $OCH_3$ | |
| $L_{12}$ | H | H | — | $CH_3$ | — | — | — | — | — | — | — | $OCH_3$ | $CH_3$ | |
| $L_{12}$ | H | H | — | H | — | — | — | — | — | — | — | $CH_3$ | $CH(OCH_3)_2$ | |
| $L_{12}$ | H | H | — | $CH_3$ | — | — | — | — | — | — | — | $CH_3$ | $OCH_3$ | |
| $L_{12}$ | H | H | — | $CHF_2$ | — | — | — | — | — | — | — | $OCH_3$ | $OCH_3$ | |
| $L_{12}$ | H | H | — | $CHF_2$ | — | — | — | — | — | — | — | $CH_3$ | $CH_3$ | |
| $L_{13}$ | H | H | — | — | H | H | — | — | 0 | — | — | $OCH_3$ | $OCH_3$ | |
| $L_{13}$ | H | H | — | — | H | H | — | — | 1 | — | — | $CH_3$ | $OCH_3$ | |
| $L_{13}$ | H | H | — | — | $CH_3$ | Cl | — | — | 0 | — | — | $OCH_3$ | $CH_3$ | |
| $L_{13}$ | $CH_3$ | H | — | — | $CH_3$ | Cl | — | — | 1 | — | — | $CH_3$ | $-CH{<}^O_O$ | |
| $L_{13}$ | H | H | — | — | $CH_3$ | $CH_3$ | — | — | 0 | — | — | $CH_3$ | $OCH_3$ | |
| $L_{13}$ | H | H | — | — | $CH_3$ | $CH_3$ | — | — | 1 | — | — | $CF_3$ | $OCH_3$ | |
| $L_{13}$ | H | H | — | — | Cl | Cl | — | — | 0 | — | — | $CH_3$ | $OCH_3$ | |
| $L_{13}$ | H | H | — | — | Cl | Cl | — | — | 1 | — | — | $OCH_3$ | $OCH_3$ | |
| $L_{14}$ | H | H | — | — | — | — | H | — | 0 | O | — | $CH_3$ | $OCH_3$ | |
| $L_{14}$ | H | H | — | — | — | — | H | — | 1 | S | — | $CH_3$ | $CH_3$ | |
| $L_{14}$ | $CH_3$ | H | — | — | — | — | $CH_3$ | — | 0 | S | — | $OCH_3$ | $OCH_3$ | |
| $L_{14}$ | H | H | — | — | — | — | $CH_3$ | — | 1 | $SO_2$ | — | $CH_3$ | $OCH_3$ | |
| $L_{14}$ | H | $CH_3$ | — | — | — | — | H | — | 1 | O | — | $CH_3$ | $CH_2OCH_2CH_3$ | |
| $L_{14}$ | H | $CH_3$ | — | — | — | — | $CH_3$ | — | 1 | $SO_2$ | — | $CF_3$ | $CH_3$ | |
| $L_{15}$ | H | H | H | — | — | — | — | — | — | O | — | $CH_3$ | $OCH_3$ | |
| $L_{15}$ | H | H | $CH_3$ | — | — | — | — | — | — | O | — | $OCH_3$ | $OCH_3$ | |
| $L_{15}$ | H | H | H | — | — | — | — | — | — | $NCH_3$ | — | $CH_3$ | $OCH_3$ | |
| $L_{15}$ | H | H | $CH_3$ | — | — | — | — | — | — | $NCH_3$ | — | $CH_3$ | $OCH_3$ | |
| $L_{15}$ | H | $CH_3$ | H | — | — | — | — | — | — | O | — | $OCH_3$ | $CH_3$ | |
| $L_{15}$ | H | $CH_3$ | H | — | — | — | — | — | — | $NCH_3$ | — | $CH_3$ | $OCH_2CH_3$ | |
| $L_{16}$ | H | H | — | H | — | — | — | — | — | — | — | $CH_3$ | $OCH_3$ | |
| $L_{16}$ | H | H | — | $CH_3$ | — | — | — | — | — | — | — | $OCH_3$ | $OCH_3$ | |
| $L_{16}$ | H | H | — | $CH_2CH_3$ | — | — | — | — | — | — | — | $CH_3$ | $OCH_3$ | |
| $L_{16}$ | H | $CH_3$ | — | H | — | — | — | — | — | — | — | $CH_3$ | $CH_3$ | |
| $L_{16}$ | H | $CH_3$ | — | $CH_3$ | — | — | — | — | — | — | — | $CH_3$ | $OCH_3$ | |
| $L_{16}$ | $CH_3$ | $CH_3$ | — | $CH_2CH_3$ | — | — | — | — | — | — | — | $CF_3$ | $CH_3$ | |
| $L_{17}$ | H | H | — | — | — | — | — | H | 0 | — | — | $OCH_3$ | $OCH_3$ | |
| $L_{17}$ | H | H | — | — | — | — | — | $CH_3$ | 0 | — | — | $CH_3$ | $OCH_3$ | |
| $L_{17}$ | H | H | — | — | — | — | — | H | 1 | — | — | $CH_3$ | $OCH_3$ | |
| $L_{17}$ | H | H | — | — | — | — | — | $CH_3$ | 1 | — | — | $OCH_3$ | $CH_3$ | |
| $L_{17}$ | H | $CH_3$ | — | — | — | — | — | H | 0 | — | — | $CH_3$ | $OCH_3$ | 191–192 |
| $L_{17}$ | H | $CH_3$ | — | — | — | — | — | H | 0 | — | — | $CH_3$ | $CH_3$ | 207–208 |
| $L_{17}$ | H | $CH_3$ | — | — | — | — | — | H | 0 | — | — | $OCH_3$ | $OCH_3$ | 202–203 |
| $L_{17}$ | H | $CH_3$ | — | — | — | — | — | H | 1 | — | — | $CH_3$ | $OCH_3$ | |
| $L_{17}$ | H | $CH_3$ | — | — | — | — | — | $CH_3$ | 0 | — | — | $OCH_3$ | $OCH_3$ | |
| $L_{17}$ | H | $CH_3$ | — | — | — | — | — | $CH_3$ | 1 | — | — | $CH_3$ | $OCH_3$ | |
| $L_{18}$ | H | H | — | — | — | — | — | H | 0 | O | — | $CH_3$ | $OCH_3$ | |

TABLE 2-continued

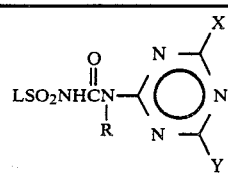

| L | R | R₁ | R₂ | R₃ | R₄ | R₅ | R₆ | R₇ | n | Q | Q₁ | X | Y | m.p. °C. |
|---|---|---|---|---|---|---|---|---|---|---|---|---|---|---|
| $L_{18}$ | H | H | — | — | — | — | — | H | 0 | $NCH_3$ | — | $OCH_3$ | $\begin{array}{c}S\\-CH\\S\end{array}$ (ring) | |
| $L_{18}$ | H | H | — | — | — | — | — | H | 1 | O | — | $CF_3$ | $OCH_3$ | |
| $L_{18}$ | H | H | — | — | — | — | — | H | 1 | $NCH_3$ | — | $OCH_3$ | $OCH_3$ | |
| $L_{18}$ | $CH_3$ | H | — | — | — | — | — | $CH_3$ | 0 | O | — | $CH_3$ | $OCH_3$ | |
| $L_{18}$ | H | H | — | — | — | — | — | $CH_3$ | 0 | $NCH_3$ | — | $CH_3$ | $OCH_3$ | |
| $L_{18}$ | H | H | — | — | — | — | — | $CH_3$ | 1 | O | — | $OCH_3$ | $OCH_3$ | |
| $L_{18}$ | H | H | — | — | — | — | — | $CH_3$ | 1 | $NCH_3$ | — | $CH_3$ | $SCH_3$ | |
| $L_{19}$ | H | H | — | — | — | — | — | — | — | — | — | $CH_3$ | $OCH_3$ | |
| $L_{19}$ | H | $CH_3$ | — | — | — | — | — | — | — | — | — | $OCH_3$ | $OCH_3$ | |
| $L_{19}$ | H | $SO_2CH_3$ | — | — | — | — | — | — | — | — | — | $CH_3$ | $OCH_3$ | |
| $L_{19}$ | H | $SO_2N(CH_3)_2$ | — | — | — | — | — | — | — | — | — | $OCH_3$ | $CH_3$ | |
| $L_{19}$ | H | $CO_2CH_3$ | — | — | — | — | — | — | — | — | — | $CH_3$ | $OCH_3$ | |
| $L_{19}$ | H | $CH_2CH=CH_2$ | — | — | — | — | — | — | — | — | — | $CH_3$ | $OCH_3$ | |
| $L_{20}$ | H | H | — | — | — | — | — | — | — | — | O | $OCH_3$ | $OCH_3$ | |
| $L_{20}$ | H | H | — | — | — | — | — | — | — | — | S | $CH_3$ | $CH_3$ | |
| $L_{20}$ | H | H | — | — | — | — | — | — | — | — | $SO_2$ | $OCH_3$ | $OCH_3$ | |
| $L_{20}$ | H | $CH_3$ | — | — | — | — | — | — | — | — | O | $CH_3$ | $OCH_3$ | |
| $L_{20}$ | H | $CH_3$ | — | — | — | — | — | — | — | — | $SO_2$ | $OCH_3$ | $SeCH_3$ | |
| $L_{20}$ | H | $SO_2CH_3$ | — | — | — | — | — | — | — | — | $SO_2$ | $CH_3$ | $OCH_3$ | |
| $L_{20}$ | H | $SO_2N(CH_3)_2$ | — | — | — | — | — | — | — | — | O | $OCH_3$ | $OCH_3$ | |
| $L_{20}$ | $CH_3$ | $SO_2N(CH_3)_2$ | — | — | — | — | — | — | — | — | $SO_2$ | $CF_3$ | $CH_3$ | |

TABLE 3

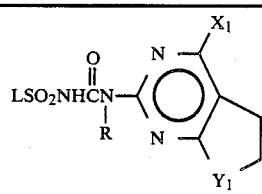

| L | R | R₁ | R₂ | R₃ | R₄ | R₅ | R₆ | R₇ | n | Q | Q₁ | X₁ | Y₁ |
|---|---|---|---|---|---|---|---|---|---|---|---|---|---|
| $L_1$ | H | H | H | — | — | — | — | — | 0 | O | — | $CH_3$ | $CH_2$ |
| $L_1$ | H | H | H | — | — | — | — | — | 0 | O | — | $CH_3$ | O |
| $L_1$ | H | $CH_3$ | H | — | — | — | — | — | 0 | O | — | $OCH_3$ | O |
| $L_1$ | H | $CH_3$ | $CH_3$ | — | — | — | — | — | 0 | O | — | $OCH_2CH_3$ | O |
| $L_1$ | H | $CH_3$ | $CH_3$ | — | — | — | — | — | 0 | O | — | $OCF_2H$ | O |
| $L_1$ | H | $CH_3$ | H | — | — | — | — | — | 1 | S | — | $CH_3$ | O |
| $L_1$ | H | $CH_3$ | H | — | — | — | — | — | 1 | $SO_2$ | — | $CH_3$ | O |
| $L_2$ | H | $CH_3$ | — | H | — | — | — | — | 0 | — | — | $CH_3$ | O |
| $L_2$ | $CH_3$ | $CH_3$ | — | $CH_3$ | — | — | — | — | 1 | — | — | $CH_3$ | O |
| $L_2$ | H | $CH_3$ | — | $CH_3$ | — | — | — | — | 1 | — | — | $CH_3$ | O |
| $L_2$ | H | $CH_3$ | — | $CHF_2$ | — | — | — | — | 0 | — | — | $CH_3$ | O |
| $L_2$ | H | H | — | H | — | — | — | — | 0 | — | — | $CH_3$ | O |
| $L_3$ | H | H | — | — | H | H | — | — | 0 | — | — | $CH_3$ | O |
| $L_3$ | H | $CH_3$ | — | — | $CH_3$ | $CH_3$ | — | — | 0 | — | — | $CH_3$ | O |
| $L_3$ | H | $CH_3$ | — | — | $CH_3$ | $CH_3$ | — | — | 1 | — | — | $CH_3$ | O |
| $L_3$ | H | $CH_3$ | — | — | Cl | Cl | — | — | 1 | — | — | $OCH_3$ | $CH_2$ |
| $L_4$ | H | H | — | — | — | — | H | — | 0 | — | O | $CH_3$ | O |
| $L_4$ | H | H | — | — | — | — | H | — | 0 | — | S | $CH_3$ | O |
| $L_4$ | H | H | — | — | — | — | H | — | 0 | — | $NCH_3$ | $CH_3$ | O |
| $L_4$ | H | $CH_3$ | — | — | — | — | H | — | 0 | — | O | $CH_3$ | O |
| $L_4$ | H | $CH_3$ | — | — | — | — | $CH_3$ | — | 0 | — | O | $OCH_3$ | O |
| $L_4$ | H | $CH_3$ | — | — | — | — | $CH_3$ | — | 1 | — | O | $CH_3$ | O |
| $L_5$ | H | $CH_3$ | H | — | — | — | — | — | — | O | — | $CH_3$ | O |
| $L_5$ | H | $CH_3$ | H | — | — | — | — | — | — | $NCH_3$ | — | $CH_3$ | O |
| $L_5$ | H | $CH_3$ | $CH_3$ | — | — | — | — | — | — | O | — | $CH_3$ | O |
| $L_5$ | H | $CH_3$ | $CH_3$ | — | — | — | — | — | — | $NCH_3$ | — | $OCH_3$ | O |
| $L_6$ | H | $CH_3$ | — | H | — | — | — | — | — | — | — | $CH_3$ | O |
| $L_6$ | H | $CH_3$ | — | $CH_3$ | — | — | — | — | — | — | — | $OCH_3$ | $CH_2$ |

TABLE 3-continued

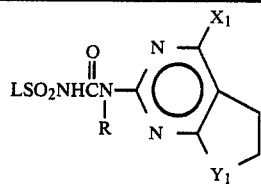

| L | R | R₁ | R₂ | R₃ | R₄ | R₅ | R₆ | R₇ | n | Q | Q₁ | X₁ | Y₁ |
|---|---|---|---|---|---|---|---|---|---|---|---|---|---|
| L₇ | H | CH₃ | — | — | — | — | — | CH₃ | 0 | — | — | CH₃ | O |
| L₇ | H | CH₃ | — | — | — | — | — | CH₃ | 1 | — | — | CH₃ | O |
| L₈ | H | CH₃ | — | — | — | — | — | CH₃ | 0 | O | — | CH₃ | O |
| L₈ | H | CH₃ | — | — | — | — | — | CH₃ | 1 | O | — | OCH₃ | O |
| L₉ | H | CH₃ | — | — | — | — | — | — | — | — | — | CH₃ | O |
| L₁₀ | H | CH₃ | — | — | — | — | — | — | — | — | O | CH₃ | O |
| L₁₁ | H | H | H | — | — | — | — | — | 0 | O | — | CH₃ | CH₂ |
| L₁₁ | H | H | CH₃ | — | — | — | — | — | 0 | S | — | OCH₃ | O |
| L₁₂ | H | H | — | CH₃ | — | — | — | — | — | — | — | CH₃ | O |
| L₁₂ | H | H | — | CH₃ | — | — | — | — | — | — | — | CH₃ | O |
| L₁₃ | H | H | — | — | H | H | — | — | 0 | — | — | CH₃ | O |
| L₁₃ | H | CH₃ | — | — | CH₃ | CH₃ | — | — | 1 | — | — | OCH₃ | O |
| L₁₄ | H | H | — | — | — | — | CH₃ | — | 0 | O | — | CH₃ | O |
| L₁₄ | H | H | — | — | — | — | CH₃ | — | 1 | O | — | CH₃ | O |
| L₁₅ | H | H | H | — | — | — | — | — | — | S | — | CH₃ | CH₂ |
| L₁₆ | H | H | — | CH₃ | — | — | — | — | — | — | — | OCH₃ | O |
| L₁₆ | H | CH₃ | — | CH₃ | — | — | — | — | — | — | — | CH₃ | O |
| L₁₇ | H | H | — | — | — | — | — | CH₃ | 0 | — | — | CH₃ | O |
| L₁₇ | H | H | — | — | — | — | — | CH₃ | 1 | — | — | CH₃ | O |
| L₁₈ | H | H | — | — | — | — | — | CH₃ | 0 | O | — | OCH₃ | O |
| L₁₈ | H | H | — | — | — | — | — | CH₃ | 1 | O | — | CH₃ | CH₂ |
| L₁₉ | H | H | — | — | — | — | — | — | — | — | — | CH₃ | O |
| L₁₉ | H | CH₃ | — | — | — | — | — | — | — | — | — | CH₃ | O |
| L₂₀ | H | H | — | — | — | — | — | — | — | — | O | CH₃ | O |
| L₂₀ | H | CH₃ | — | — | — | — | — | — | — | — | O | OCH₃ | O |

TABLE 4

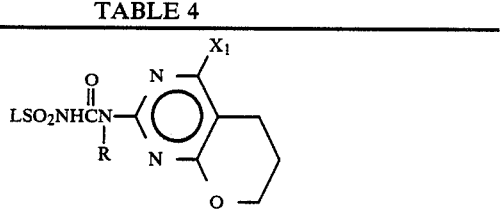

| L | R | R₁ | R₂ | R₃ | R₄ | R₅ | R₆ | R₇ | n | Q | Q₁ | X₁ |
|---|---|---|---|---|---|---|---|---|---|---|---|---|
| L₁ | H | CH₃ | H | — | — | — | — | — | 0 | 0 | — | CH₃ |
| L₁ | H | CH₃ | H | — | — | — | — | — | 0 | 0 | — | OCH₃ |
| L₁ | H | CH₃ | H | — | — | — | — | — | 0 | 0 | — | OCH₂CH₃ |
| L₁ | H | CH₃ | H | — | — | — | — | — | 1 | 0 | — | OCF₂H |
| L₂ | H | CH₃ | — | CH₃ | — | — | — | — | 0 | — | — | CH₃ |
| L₂ | H | CH₃ | — | CH₃ | — | — | — | — | 1 | — | — | CH₃ |
| L₃ | H | CH₃ | — | — | H | H | — | — | 0 | — | — | OCH₃ |
| L₃ | H | CH₃ | — | — | H | H | — | — | 1 | — | — | CH₃ |
| L₄ | H | CH₃ | — | — | — | — | CH₃ | — | 0 | — | O | CH₃ |
| L₄ | H | CH₃ | — | — | — | — | CH₃ | — | 1 | — | O | OCH₃ |
| L₅ | H | CH₃ | H | — | — | — | — | — | — | 0 | — | CH₃ |
| L₆ | H | CH₃ | — | CH₃ | — | — | — | — | — | — | — | CH₃ |
| L₇ | H | CH₃ | — | — | — | — | — | CH₃ | 0 | — | — | OCH₃ |
| L₇ | H | CH₃ | — | — | — | — | — | CH₃ | 1 | — | — | CH₃ |
| L₈ | H | CH₃ | — | — | — | — | — | CH₃ | 0 | 0 | — | CH₃ |
| L₈ | H | CH₃ | — | — | — | — | — | CH₃ | 1 | 0 | — | CH₃ |
| L₉ | H | CH₃ | — | — | — | — | — | — | — | — | — | OCH₃ |
| L₁₀ | H | CH₃ | — | — | — | — | — | — | — | — | O | CH₃ |
| L₁₁ | H | H | H | — | — | — | — | — | 0 | 0 | — | CH₃ |
| L₁₁ | H | H | H | — | — | — | — | — | 0 | 1 | — | CH₃ |
| L₁₂ | H | H | — | CH₃ | — | — | — | — | — | — | — | OCH₃ |
| L₁₂ | H | H | — | CH₃ | — | — | — | — | — | — | — | CH₃ |
| L₁₃ | H | H | — | — | H | H | — | — | 0 | — | — | CH₃ |
| L₁₃ | H | H | — | — | H | H | — | — | 1 | — | — | OCH₃ |
| L₁₄ | H | H | — | — | — | — | CH₃ | — | 0 | — | O | CH₃ |
| L₁₄ | H | H | — | — | — | — | CH₃ | — | 1 | — | S | CH₃ |
| L₁₅ | H | H | H | — | — | — | — | — | — | 0 | — | CH₃ |
| L₁₆ | H | H | — | CH₃ | — | — | — | — | — | — | — | OCH₃ |
| L₁₇ | H | H | — | — | — | — | — | CH₃ | 0 | — | — | CH₃ |
| L₁₇ | H | H | — | — | — | — | — | CH₃ | 1 | — | — | CH₃ |
| L₁₈ | H | H | — | — | — | — | — | CH₃ | 0 | 0 | — | OCH₃ |

TABLE 4-continued

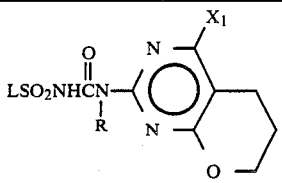

| L | R | R₁ | R₂ | R₃ | R₄ | R₅ | R₆ | R₇ | n | Q | Q₁ | X₁ |
|---|---|----|----|----|----|----|----|----|---|---|----|-----|
| L₁₈ | H | H | — | — | — | — | — | CH₃ | 1 | 0 | — | CH₃ |
| L₁₉ | H | H | — | — | — | — | — | — | — | — | — | CH₃ |
| L₂₀ | H | H | — | — | — | — | — | — | — | — | O | OCH₃ |

TABLE 5

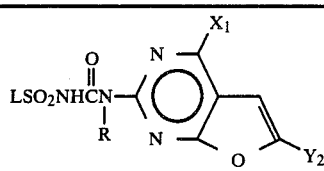

| L | R | R₁ | R₂ | R₃ | R₄ | R₅ | R₆ | R₇ | n | Q | Q₁ | X₁ | Y₂ |
|---|---|----|----|----|----|----|----|----|---|---|----|-----|-----|
| L₁ | H | CH₃ | H | — | — | — | — | — | 0 | 0 | — | CH₃ | H |
| L₁ | H | CH₃ | H | — | — | — | — | — | 1 | 0 | — | CH₃ | CH₃ |
| L₂ | H | CH₃ | — | CH₃ | — | — | — | — | 0 | — | — | CH₃ | CH₃ |
| L₂ | H | CH₃ | — | CH₃ | — | — | — | — | 1 | — | — | OCH₃ | CH₃ |
| L₃ | H | CH₃ | — | — | H | H | — | — | 0 | — | — | CH₃ | CH₃ |
| L₃ | H | CH₃ | — | — | CH₃ | CH₃ | — | — | 1 | — | — | CH₃ | H |
| L₄ | H | CH₃ | — | — | — | — | CH₃ | — | 0 | — | O | OCH₃ | CH₃ |
| L₄ | H | CH₃ | — | — | — | — | CH₃ | — | 1 | — | O | CH₃ | CH₃ |
| L₅ | H | CH₃ | H | — | — | — | — | — | — | 0 | — | CH₃ | CH₃ |
| L₆ | H | CH₃ | — | CH₃ | — | — | — | — | — | — | — | CH₃ | CH₃ |
| L₆ | H | CH₃ | — | CH₃ | — | — | — | — | — | — | — | OCH₃ | CH₃ |
| L₆ | H | CH₃ | — | CH₃ | — | — | — | — | — | — | — | OCH₂CH₃ | H |
| L₆ | H | CH₃ | — | CH₃ | — | — | — | — | — | — | — | OCF₂H | CH₃ |
| L₇ | H | CH₃ | — | — | — | — | — | CH₃ | 0 | — | — | CH₃ | CH₃ |
| L₇ | H | CH₃ | — | — | — | — | — | CH₃ | 1 | — | — | CH₃ | CH₃ |
| L₈ | H | CH₃ | — | — | — | — | — | CH₃ | 0 | 0 | — | OCH₃ | H |
| L₈ | H | CH₃ | — | — | — | — | — | CH₃ | 1 | 0 | — | CH₃ | CH₃ |
| L₉ | H | CH₃ | — | — | — | — | — | — | — | — | — | CH₃ | CH₃ |
| L₁₀ | H | CH₃ | — | — | — | — | — | — | — | — | O | OCH₃ | CH₃ |
| L₁₁ | H | H | H | — | — | — | — | — | 0 | 0 | — | CH₃ | CH₃ |
| L₁₁ | H | H | H | — | — | — | — | — | 0 | 1 | — | CH₃ | H |
| L₁₂ | H | H | — | CH₃ | — | — | — | — | — | — | — | CH₃ | CH₃ |
| L₁₂ | H | H | — | CH₃ | — | — | — | — | — | — | — | OCH₃ | CH₃ |
| L₁₃ | H | H | — | — | H | H | — | — | 0 | — | — | CH₃ | CH₃ |
| L₁₃ | H | H | — | — | CH₃ | CH₃ | — | — | 1 | — | — | CH₃ | H |
| L₁₄ | H | H | — | — | — | — | CH₃ | — | 0 | — | O | OCH₃ | CH₃ |
| L₁₄ | H | H | — | — | — | — | CH₃ | — | 1 | — | SO₂ | CH₃ | CH₃ |
| L₁₅ | H | H | H | — | — | — | — | — | — | 0 | — | CH₃ | H |
| L₁₆ | H | H | — | CH₃ | — | — | — | — | — | — | — | OCH₃ | CH₃ |
| L₁₇ | H | H | — | — | — | — | — | CH₃ | 0 | — | — | CH₃ | CH₃ |
| L₁₇ | H | H | — | — | — | — | — | CH₃ | 1 | — | — | CH₃ | H |
| L₁₈ | H | H | — | — | — | — | — | CH₃ | 0 | 0 | — | OCH₃ | CH₃ |
| L₁₈ | H | H | — | — | — | — | — | CH₃ | 1 | 0 | — | CH₃ | CH₃ |
| L₁₉ | H | H | — | — | — | — | — | — | — | — | — | CH₃ | CH₃ |
| L₂₀ | H | H | — | — | — | — | — | — | — | — | O | OCH₃ | H |

TABLE 6

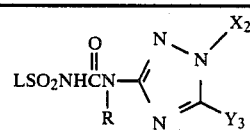

| L | R | R₁ | R₂ | R₃ | R₄ | R₅ | R₆ | R₇ | n | Q | Q₁ | X₂ | Y₂ |
|---|---|----|----|----|----|----|----|----|---|---|----|-----|-----|
| L₁ | H | CH₃ | H | — | — | — | — | — | 0 | O | — | CH₃ | OCH₂CH₃ |
| L₁ | H | CH₃ | H | — | — | — | — | — | 0 | O | — | CH₂CH₃ | OCH₃ |
| L₁ | H | CH₃ | H | — | — | — | — | — | 0 | O | — | CH₂CF₃ | SCH₃ |
| L₁ | H | CH₃ | H | — | — | — | — | — | 1 | O | — | CH₃ | CH₃ |
| L₁ | H | CH₃ | H | — | — | — | — | — | 0 | O | — | CH₃ | CH₂CH₃ |
| L₂ | H | CH₃ | — | CH₃ | — | — | — | — | 0 | — | — | CH₃ | OCH₃ |
| L₂ | H | CH₃ | — | CH₃ | — | — | — | — | 1 | — | — | CH₃ | OCH₃ |

TABLE 6-continued $$LSO_2NHCN\underset{R}{\overset{\overset{O}{\|}}{-}}\diagup\overset{N\diagdown N\diagup X_2}{\underset{N\diagdown Y_3}{}}$$

| L | R | $R_1$ | $R_2$ | $R_3$ | $R_4$ | $R_5$ | $R_6$ | $R_7$ | n | Q | $Q_1$ | $X_2$ | $Y_2$ |
|---|---|---|---|---|---|---|---|---|---|---|---|---|---|
| $L_3$ | H | $CH_3$ | — | — | H | H | — | — | 0 | — | — | $CH_3$ | $OCH_3$ |
| $L_4$ | H | $CH_3$ | — | — | — | — | $CH_3$ | — | 0 | — | O | $CH_3$ | $OCH_3$ |
| $L_5$ | H | $CH_3$ | H | — | — | — | — | — | — | O | — | $CH_3$ | $OCH_3$ |
| $L_6$ | H | $CH_3$ | — | $CH_3$ | — | — | — | — | — | — | — | $CH_3$ | $OCH_3$ |
| $L_7$ | H | $CH_3$ | — | — | — | — | — | $CH_3$ | 1 | — | — | $CH_2CH_3$ | $OCH_3$ |
| $L_8$ | H | $CH_3$ | — | — | — | — | — | $CH_3$ | 0 | O | — | $CH_3$ | $OCH_3$ |
| $L_9$ | H | $CH_3$ | — | — | — | — | — | — | — | — | — | $CH_3$ | $OCH_2CH_3$ |
| $L_{10}$ | H | $CH_3$ | — | — | — | — | — | — | — | — | O | $CH_3$ | $OCH_3$ |
| $L_{11}$ | H | H | H | — | — | — | — | — | 0 | S | — | $CH_3$ | $OCH_3$ |
| $L_{12}$ | H | H | — | $CH_3$ | — | — | — | — | — | — | — | $CH_2CF_3$ | $OCH_3$ |
| $L_{12}$ | H | H | — | $CH_3$ | — | — | — | — | — | — | — | $CH_3$ | $OCH_3$ |
| $L_{13}$ | H | H | — | — | H | H | — | — | 0 | — | — | $CH_3$ | $OCH_3$ |
| $L_{13}$ | H | H | — | — | $CH_3$ | $CH_3$ | — | — | 1 | — | — | $CH_3$ | $OCH_3$ |
| $L_{14}$ | H | H | — | — | — | — | $CH_3$ | — | 0 | — | O | $CH_3$ | $OCH_3$ |
| $L_{14}$ | H | H | — | — | — | — | $CH_3$ | — | 1 | — | $SO_2$ | $CH_3$ | $OCH_3$ |
| $L_{15}$ | H | H | H | — | — | — | — | — | — | O | — | $CH_3$ | $SCH_3$ |
| $L_{16}$ | H | H | — | $CH_3$ | — | — | — | — | — | — | — | $CH_2CH_3$ | $OCH_3$ |
| $L_{17}$ | H | H | — | — | — | — | — | $CH_3$ | 0 | — | — | $CH_3$ | $OCH_3$ |
| $L_{17}$ | H | H | — | — | — | — | — | $CH_3$ | 1 | — | — | $CH_3$ | $OCH_3$ |
| $L_{18}$ | H | H | — | — | — | — | — | $CH_3$ | 0 | O | — | $CH_2CF_3$ | $OCH_3$ |
| $L_{18}$ | H | H | — | — | — | — | — | $CH_3$ | 1 | O | — | $CH_3$ | $OCH_3$ |
| $L_{19}$ | H | H | — | — | — | — | — | — | — | — | — | $CH_3$ | $OCH_3$ |
| $L_{20}$ | H | H | — | — | — | — | — | — | — | — | O | $CH_3$ | $CH_2CH_3$ |

TABLE 7

$$LSO_2NHCNCH_2\underset{R}{\overset{\overset{O}{\|}}{-}}\diagup\overset{N\diagup OCH_3}{\underset{N\diagdown X_3}{\diagdown N}}$$

| L | R | $R_1$ | $R_2$ | $R_3$ | $R_4$ | $R_5$ | $R_6$ | $R_7$ | n | Q | $Q_1$ | $X_3$ |
|---|---|---|---|---|---|---|---|---|---|---|---|---|
| $L_1$ | H | $CH_3$ | H | — | — | — | — | — | 0 | 0 | — | $CH_3$ |
| $L_1$ | H | $CH_3$ | H | — | — | — | — | — | 1 | 0 | — | $OCH_3$ |
| $L_2$ | H | $CH_3$ | — | $CH_3$ | — | — | — | — | 0 | — | — | $CH_3$ |
| $L_2$ | H | $CH_3$ | — | $CH_3$ | — | — | — | — | 1 | — | — | $CH_3$ |
| $L_3$ | H | $CH_3$ | — | — | H | H | — | — | 0 | — | — | $CH_3$ |
| $L_4$ | H | $CH_3$ | — | — | — | — | $CH_3$ | — | 0 | — | O | $OCH_3$ |
| $L_5$ | H | $CH_3$ | H | — | — | — | — | — | — | O | — | $CH_3$ |
| $L_6$ | H | $CH_3$ | — | $CH_3$ | — | — | — | — | — | — | — | $CH_3$ |
| $L_7$ | H | $CH_3$ | — | — | — | — | — | $CH_3$ | 0 | — | — | $OCH_3$ |
| $L_7$ | H | $CH_3$ | — | — | — | — | — | $CH_3$ | 1 | — | — | $CH_3$ |
| $L_8$ | H | $CH_3$ | — | — | — | — | — | $CH_3$ | 0 | 0 | — | $CH_3$ |
| $L_8$ | H | $CH_3$ | — | — | — | — | — | $CH_3$ | 1 | 0 | — | $CH_3$ |
| $L_9$ | H | $CH_3$ | — | — | — | — | — | — | — | — | — | $OCH_3$ |
| $L_{10}$ | H | $CH_3$ | — | — | — | — | — | — | — | — | O | $CH_3$ |
| $L_{11}$ | H | H | H | — | — | — | — | — | 0 | 0 | — | $CH_3$ |
| $L_{11}$ | H | H | H | — | — | — | — | — | 0 | 1 | — | $CH_3$ |
| $L_{12}$ | H | H | — | $CH_3$ | — | — | — | — | — | — | — | $OCH_3$ |
| $L_{12}$ | H | H | — | $CH_3$ | — | — | — | — | — | — | — | $CH_3$ |
| $L_{13}$ | H | H | — | — | H | H | — | — | 0 | — | — | $CH_3$ |
| $L_{13}$ | H | H | — | — | $CH_3$ | $CH_3$ | — | — | 1 | — | — | $OCH_3$ |
| $L_{14}$ | H | H | — | — | — | — | $CH_3$ | — | 0 | — | O | $CH_3$ |
| $L_{14}$ | H | H | — | — | — | — | $CH_3$ | — | 1 | — | $SO_2$ | $CH_3$ |
| $L_{15}$ | H | H | H | — | — | — | — | — | — | 0 | — | $OCH_3$ |
| $L_{16}$ | H | H | — | $CH_3$ | — | — | — | — | — | — | — | $CH_3$ |
| $L_{17}$ | H | H | — | — | — | — | — | $CH_3$ | 0 | — | — | $CH_3$ |
| $L_{17}$ | H | H | — | — | — | — | — | $CH_3$ | 1 | — | — | $OCH_3$ |
| $L_{18}$ | H | H | — | — | — | — | — | $CH_3$ | 0 | 0 | — | $OCH_3$ |
| $L_{18}$ | H | H | — | — | — | — | — | $CH_3$ | 1 | 0 | — | $CH_3$ |
| $L_{19}$ | H | H | — | — | — | — | — | — | — | — | — | $OCH_3$ |
| $L_{20}$ | H | H | — | — | — | — | — | — | — | — | O | $CH_3$ |

FORMULATIONS

Useful formulations of the compounds of Formula 1 can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 8

| | Active Ingredient | Weight Percent* | |
|---|---|---|---|
| | | Diluent(s) | Surfactant(s) |
| Wettable Powders | 20-90 | 0-74 | 1-10 |
| Oil Suspension, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 5

Wettable Powder

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 6

Wettable Powder

| | |
|---|---|
| N—[(4,6-dimethoxypyrimidin-2-yl)aminocarbonyl]-2,4,6,7-tetrahydro-2-methyl-4-oxopyrano[4,3-c]pyrazole-3-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 7

Granule

| | |
|---|---|
| Wettable Powder of Example 6 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 8

Extruded Pellet

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Oil Suspension

| | |
|---|---|
| N—[(4,6-dimethoxypyrimidin-2-yl)aminocarbonyl]-2,4,6,7-tetrahydro-2-methyl-4-oxopyrano[4,3-c]pyrazole-3-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 10

Wettable Powder

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 20% |
| sodium alkylnaphthalenesulfonate | 4% |
| sodium ligninsulfonate | 4% |
| low viscosity methyl cellulose | 3% |

| | |
|---|---|
| attapulgite | 69% |

-continued

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 11

Low Strength Granule

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 12

Aqueous Suspension

| | |
|---|---|
| N—[(4,6-dimethoxypyrimidin-2-yl)aminocarbonyl]-2,4,6,7-tetrahydro-2-methyl-4-oxopyrano[4,3-c]-pyrazole-3-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

Solution

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide, sodium salt | 5% |
| water | 95% |

The salt is added directly to the water with stirring to produce the solution, which may then be packaged for use.

EXAMPLE 14

Low Strength Granule

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 15

Granule

| | |
|---|---|
| N—[(4,6-dimethoxypyrimidin-2-yl)aminocarbonyl]-2,4,6,7-tetrahydro-2-methyl-4-oxopyrano[4,3-c]-pyrazole-3-sulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 16

High Strength Concentrate

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 17

Wettable Powder

| | |
|---|---|
| N—[(4,6-dimethoxypyrimidin-2-yl)aminocarbonyl]-2,4,6,7-tetrahydro-2-methyl-4-oxopyrano[4,3-c]-pyrazole-3-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 18

Wettable Powder

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

Oil Suspension

| | |
|---|---|
| N—[(4,6-dimethoxypyrimidin-2-yl)aminocarbonyl]-4,6-dihydro-2-methyl-4-oxo-2H—furo[3,4-c]pyrazole-3-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 20

Dust

| | |
|---|---|
| N—[(4,6-dimethoxypyrimidin-2-yl)aminocarbonyl]-2,4,6,7-tetrahydro-2-methyl-4-oxopyrano[4,3-c]-pyrazole-3-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

Test results indicate that the compounds of the present invention are active herbicides as pre-emergent or post-emergent herbicides or plant growth regulants. Many of them have utility for broadspectrum pre- and-/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, especially wheat and rice.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistance is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria sp.), barnyardgrass (*Echinochloa crusgalli*), cheatgrass *Bromus secalinus*), wild oats (*Avena fatua*), sicklepod (*Cassia obtusifolia*), velvet leaf (*Abutilon theophrasti*), morningglory (Ipomoea sp.), cocklebur (Xanthium sp.), sorghum, corn, soybean, sugarbeet, cotton, rice, wheat and purple nutsedge (*Cyperus rotundus*) were planted and treated pre-emergence with the chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

| Compound | X | Y | Z |
|---|---|---|---|
| 1 | CH$_3$ | CH$_3$ | CH |
| 2 | OCH$_3$ | CH$_3$ | CH |
| 3 | OCH$_3$ | OCH$_3$ | CH |
| 4 | Cl | OCH$_3$ | CH |
| 5 | CH$_3$ | OCH$_3$ | N |
| 6 | OCH$_3$ | OCH$_3$ | N |

| 7 | OCH$_3$ | OCH$_3$ | N |
| 8 | OCH$_3$ | CH$_3$ | N |
| 9 | Cl | OCH$_3$ | CH |
| 10 | CH$_3$ | CH$_3$ | CH |
| 11 | OCH$_3$ | OCH$_3$ | CH |
| 12 | CH$_3$ | CH$_3$ | N |
| 13 | OCH$_3$ | CH$_3$ | CH |

TABLE A

Rate 0.05 (kg/ha)

| | Compound 1 | Compound 2 | Compound 3 | Compound 4 | Compound 5 | Compound 6 | Compound 7 | Compound 8 |
|---|---|---|---|---|---|---|---|---|
| POSTEMERGENCE | | | | | | | | |
| Morningglory | 0 | 3G | 2C,5G | 0 | 0 | 0 | 0 | 0 |
| Cocklebur | 0 | 3C,9G | 10C | 9H | 0 | 0 | 0 | 0 |
| Velvetleaf | 2G | 2C,6G | 4C,9G | 0 | 0 | 0 | — | — |
| Nutsedge | 0 | 0 | 3C,9G | 0 | 0 | 0 | 0 | 0 |
| Crabgrass | 0 | 2C | 8G | 0 | 0 | 0 | 0 | 0 |
| Barnyardgrass | 0 | 2C | 3C,9H | 0 | 0 | 0 | 0 | 0 |
| Cheatgrass | 0 | 0 | 5G | 0 | 0 | 0 | 0 | 0 |
| Wild Oats | 0 | 0 | 0 | 0 | 0 | 0 | 0 | 0 |
| Wheat | 0 | 0 | 0 | 0 | 0 | 0 | 0 | 0 |
| Corn | 0 | 5H | 2C,9H | 0 | 3C,9G | 3C,8H | 0 | 0 |
| Soybean | 0 | 3H | 2C,9G | 0 | 0 | 0 | 0 | 0 |
| Rice | 0 | 2G | 5G | 0 | 7G | 2C,9G | 0 | 0 |
| Sorghum | 0 | 3C | 2C,7H | 0 | 3C,9H | 3H,9H | 0 | 0 |
| Sugar Beets | 0 | 3C,7H | 3C,9G | 3H | 0 | 0 | 0 | 0 |
| Cotton | 0 | 3C,8H | 9G | 0 | 0 | 0 | 0 | 0 |
| Cassia | | | | | | | | |
| PREEMERGENCE | | | | | | | | |
| Morningglory | 0 | 5G | 8G | 0 | 0 | 0 | 0 | 0 |
| Cocklebur | 0 | 8G | 7H | 5H | 0 | 0 | 0 | 0 |
| Velvetleaf | 0 | 7G | 5C,9G | 2G | 0 | 0 | — | — |
| Nutsedge | 0 | 0 | 3G | 0 | 0 | 0 | 0 | 0 |
| Crabgrass | 0 | 3G | 0 | 0 | 0 | 0 | 0 | 0 |
| Barnyardgrass | 0 | 2G | 6H | 0 | 0 | 0 | 0 | 0 |
| Cheatgrass | 0 | 0 | 5G | 0 | 0 | 0 | 0 | 0 |
| Wild Oats | 0 | 0 | 0 | 0 | 0 | 0 | 0 | 0 |
| Wheat | 0 | 0 | 0 | 0 | 0 | 0 | 0 | 0 |
| Corn | 0 | 3G | 3C,6H | 0 | 2C,5G | 0 | 0 | 0 |
| Soybean | 0 | 2C | 3C,5G | 0 | 0 | 0 | 0 | 0 |
| Rice | 0 | 5G | 2G | 3G | 0 | 0 | 0 | 0 |
| Sorghum | 0 | 0 | 3C,6G | 0 | 0 | 0 | 0 | 0 |
| Sugar Beets | 0 | 3C,8G | 5C,9G | 1H | 0 | 0 | 0 | 0 |
| Cotton | 0 | 3C,5G | 9G | 2G | 0 | 0 | 0 | 0 |
| Cassia | | | | | | | | 0 |

| | Compound 9 | Compound 10 | Compound 11 | Compound 12 | Compound 13 |
|---|---|---|---|---|---|
| POSTEMERGENCE | | | | | |
| Morningglory | 0 | 0 | 2C,5G | 0 | 0 |
| Cocklebur | 0 | 0 | 2H | 0 | 2H |
| Velvetleaf | — | — | — | — | — |
| Nutsedge | 0 | 0 | 0 | 0 | 0 |
| Crabgrass | 0 | 0 | 0 | 0 | 0 |
| Barnyardgrass | 0 | 0 | 0 | 0 | 0 |
| Cheatgrass | 0 | 0 | 0 | 0 | 0 |
| Wild Oats | 0 | 0 | 0 | 0 | 0 |
| Wheat | 0 | 0 | 0 | 0 | 0 |
| Corn | 0 | 0 | 0 | 0 | 0 |
| Soybean | 0 | 0 | 3C,7G | 0 | 1H |
| Rice | 0 | 0 | 0 | 0 | 0 |
| Sorghum | 0 | 0 | 0 | 0 | 0 |
| Sugar Beets | 0 | 0 | 3C,8G | 0 | 4C,9G |
| Cotton | 0 | 0 | 4C,8G | 0 | 2C,5G |
| Cassia | 0 | 0 | 1C | 0 | 1H |
| PREEMERGENCE | | | | | |
| Morningglory | 0 | 0 | 8G | 0 | 0 |
| Cocklebur | 0 | 0 | 8H | 0 | 3H |
| Velvetleaf | — | — | — | — | — |
| Nutsedge | 0 | 0 | 0 | 0 | 5G |
| Crabgrass | 0 | 0 | 0 | 0 | 0 |
| Barnyardgrass | 0 | 0 | 0 | 0 | 0 |
| Cheatgrass | 0 | 0 | 0 | 0 | 0 |
| Wild Oats | 0 | 0 | 0 | 0 | 0 |
| Wheat | 0 | 0 | 0 | 0 | 0 |
| Corn | 0 | 0 | 2C,7G | 0 | 1C |
| Soybean | 0 | 0 | 0 | 0 | 1C |
| Rice | 0 | 0 | 0 | 0 | 2G |
| Sorghum | 0 | 0 | 2C | 0 | 1C |
| Sugar Beets | 0 | 0 | 2C,7G | 0 | 4C,5H |
| Cotton | 0 | 0 | 3G | 0 | 0 |
| Cassia | 0 | 0 | 0 | 0 | 0 |

It is noted that certain compounds tested were inactive at the low rates tested. It is thought they would demonstrate activity at higher testing rates.

What is claimed is:

1. A compound selected from

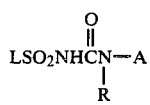

wherein
R is H or CH₃;
L is

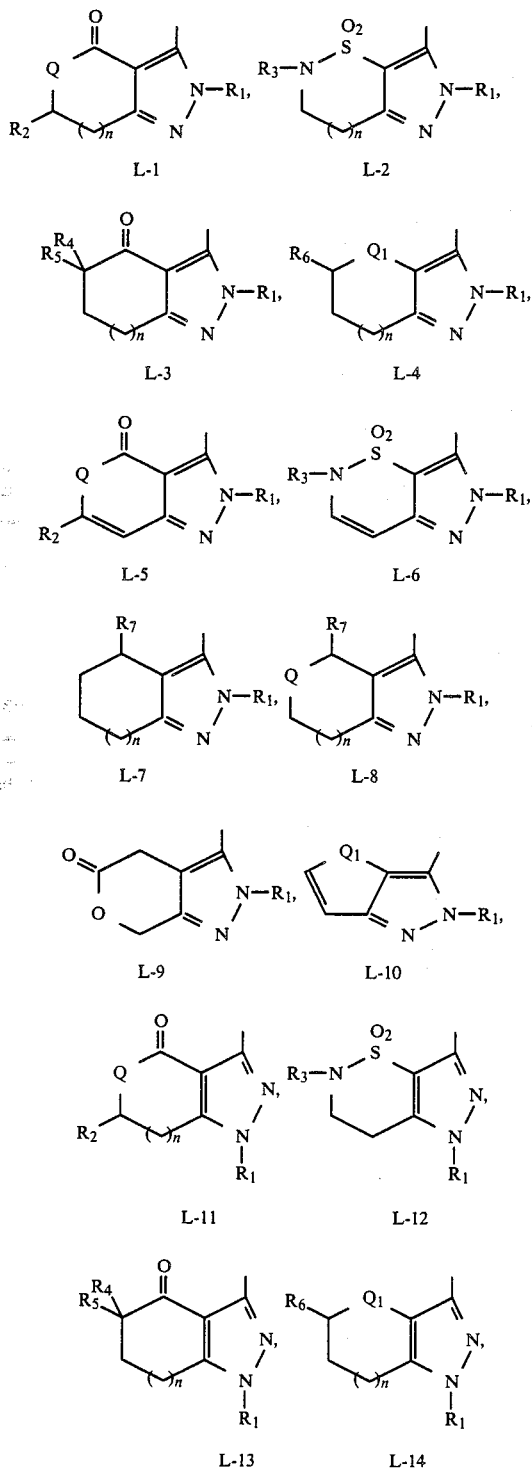

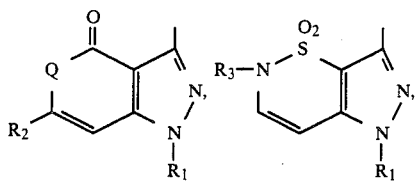

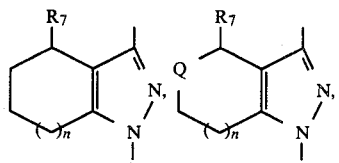

$R_1$ is H, $C_1$-$C_3$ alkyl, $CH_2CH=CH_2$, $CH_2C\equiv CH$, $CH_2CF_3$, $CHF_2$, phenyl, phenyl substituted with $NO_2$, $CH_3$, $OCH_3$, Cl, Br or F,

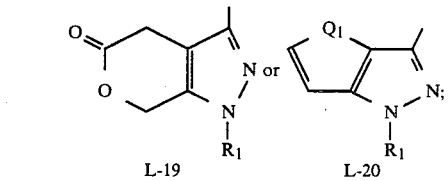

$SO_2CH_3$, $SO_2N(CH_3)_2$ or $CO_2CH_3$;
$R_2$ is H or $C_1$-$C_3$ alkyl;
$R_3$ is H, $C_1$-$C_3$ alkyl or $CHF_2$;
$R_4$ is H, Cl or $CH_3$;
$R_5$ is H, Cl or $CH_3$;
$R_6$ is H or $C_1$-$C_3$ alkyl;
$R_7$ is H or $CH_3$;
n is 0 or 1;
Q is O, S or $NCH_3$;
$Q_1$ is O, S or $SO_2$;
A is

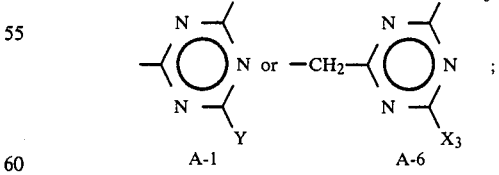

X is $CH_3$, $OCH_3$, $OC_2H_5$, $CF_3$, or $CFH_2$;
Y is H, $C_1$-$C_3$ alkyl, $OCH_3$, $OCH_2CH_3$, $CH_2OCH_3$, $SeCH_3$, $CH_2OCH_2CH_3$, $NH_2$, $NHCH_3$, $N(CH_3)_2$, $CF_3$, $SCH_3$, $OCH_2CH=CH_2$, $OCH_2C\equiv CH$, $OCH_2CF_3$, $OCH_2CH_2OCH_3$, $CH_2SCH_3$, $SCF_2H$, cyclopropyl, $CR_8(WCH_3)_2$,

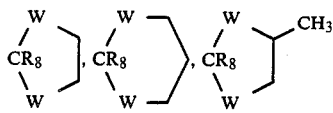

or CR$_8$(WCH$_2$CH$_3$)$_2$;
R$_8$ is H or CH$_3$;
W is O or S;
Z is N; X$_3$ is CH$_3$ or OCH$_3$;
provided that when Y is SeCH$_3$, then X is CH$_3$, OCH$_3$, OCH$_2$CH$_3$, or CF$_3$.

2. A compound of claim 1 where A is A-1 and R is H.
3. A compound of claim 2 where X is CH$_3$, OCH$_3$ or Cl and Y is C$_1$-C$_3$ alkyl, OCH$_3$, OC$_2$H$_5$, CH$_2$OCH$_3$, CF$_3$, OCH$_2$CF$_3$, CH(OCH$_3$)$_2$ or cyclopropyl.
4. A compound of claim 3 where L is L-1, L-2, L-3, L-4, L-5, L-6, L-7, L-8, L-9 or L-10.
5. A compound of claim 4 where R$_1$ is H or C$_1$-C$_3$ alkyl, R$_2$ is H or CH$_3$, R$_3$ is CH$_3$, R$_4$ is H or CH$_3$, R$_5$ is H or CH$_3$, R$_6$ is H or CH$_3$, R$_7$ is H and Q is O.
6. A compound of claim 5 where L is L-1.
7. A compound of claim 5 where L is L-2.
8. A compound of claim 5 where L is L-3.
9. A compound of claim 5 where L is L-4.
10. A compound of claim 5 where L is L-5.
11. A compound of claim 5 where L is L-6.
12. A compound of claim 5 where L is L-7.
13. A compound of claim 5 where L is L-8.
14. A compound of claim 5 where L is L-9.
15. A compound of claim 5 where L is L-10.
16. A composition suitable for controlling the growth of undesired vegetation which comprises an effective amount of a compound of claim 1 and at least one of the following: surfactant, solid or liquid diluent.
17. A composition suitable for controlling the growth of undesired vegetation which comprises an effective amount of a compound of claim 2 and at least one of the following: surfactant, solid or liquid diluent.
18. A composition suitable for controlling the growth of undesired vegetation which comprises an effective amount of a compound of claim 3 and at least one of the following: surfactant, solid or liquid diluent.
19. A composition suitable for controlling the growth of undesired vegetation which comprises an effective amount of a compound of claim 4 and at least one of the following: surfactant, solid or liquid diluent.
20. A composition suitable for controlling the growth of undesired vegetation which comprises an effective amount of a compound of claim 5 and at least one of the following: surfactant, solid or liquid diluent.
21. A composition suitable for controlling the growth of undesired vegetation which comprises an effective amount of a compound of claim 6 and at least one of the following: surfactant, solid or liquid diluent.
22. A composition suitable for controlling the growth of undesired vegetation which comprises an effective amount of a compound of claim 7 and at least one of the following: surfactant, solid or liquid diluent.
23. A composition suitable for controlling the growth of undesired vegetation which comprises an effective amount of a compound of claim 8 and at least one of the following: surfactant, solid or liquid diluent.
24. A composition suitable for controlling the growth of undesired vegetation which comprises an effective amount of a compound of claim 9 and at least one of the following: surfactant, solid or liquid diluent.
25. A composition suitable for controlling the growth of undesired vegetation which comprises an effective amount of a compound of claim 10 and at least one of the following: surfactant, solid or liquid diluent.
26. A composition suitable for controlling the growth of undesired vegetation which comprises an effective amount of a compound of claim 11 and at least one of the following: surfactant, solid or liquid diluent.
27. A composition suitable for controlling the growth of undesired vegetation which comprises an effective amount of a compound of claim 12 and at least one of the following: surfactant, solid or liquid diluent.
28. A composition suitable for controlling the growth of undesired vegetation which comprises an effective amount of a compound of claim 13 and at least one of the following: surfactant, solid or liquid diluent.
29. A composition suitable for controlling the growth of undesired vegetation which comprises an effective amount of a compound of claim 14 and at least one of the following: surfactant, solid or liquid diluent.
30. A composition suitable for controlling the growth of undesired vegetation which comprises an effective amount of a compound of claim 15 and at least one of the following: surfactant, solid or liquid diluent.
31. A method for controlling the growth of undesired vegetation which comprises applying to the locus to be protected an effective amount of a compound of claim 1.
32. A method for controlling the growth of undesired vegetation which comprises applying to the locus to be protected an effective amount of a compound of claim 2.
33. A method for controlling the growth of undesired vegetation which comprises applying to the locus to be protected an effective amount of a compound of claim 3.
34. A method for controlling the growth of undesired vegetation which comprises applying to the locus to be protected an effective amount of a compound of claim 4.
35. A method for controlling the growth of undesired vegetation which comprises applying to the locus to be protected an effective amount of a compound of claim 5.
36. A method for controlling the growth of undesired vegetation which comprises applying to the locus to be protected an effective amount of a compound of claim 6.
37. A method for controlling the growth of undesired vegetation which comprises applying to the locus to be protected an effective amount of a compound of claim 7.
38. A method for controlling the growth of undesired vegetation which comprises applying to the locus to be protected an effective amount of a compound of claim 8.
39. A method for controlling the growth of undesired vegetation which comprises applying to the locus to be protected an effective amount of a compound of claim 9.
40. A method for controlling the growth of undesired vegetation which comprises applying to the locus to be protected an effective amount of a compound of claim 10.
41. A method for controlling the growth of undesired vegetation which comprises applying to the locus to be protected an effective amount of a compound of claim 11.

42. A method for controlling the growth of undesired vegetation which comprises applying to the locus to be protected an effective amount of a compound of claim 12.

43. A method for controlling the growth of undesired vegetation which comprises applying to the locus to be protected an effective amount of a compound of claim 13.

44. A method for controlling the growth of undesired vegetation which comprises applying to the locus to be protected an effective amount of a compound of claim 14.

45. A method for controlling the growth of undesired vegetation which comprises applying to the locus to be protected an effective amount of a compound of claim 15.

* * * * *